US007575860B2

(12) United States Patent
Evans et al.

(10) Patent No.: US 7,575,860 B2
(45) Date of Patent: Aug. 18, 2009

(54) DNA JOINING METHOD

(76) Inventors: David H. Evans, 1 William Street, Carlisle, Ontario (CA) L0R 1H2; David O. Willer, 55 Koch Drive, Guelph, Ontario (CA) N1G 4G7; Xiao-Dan Yao, 45-252 Stone Road West, Guelph, Ontario (CA) N1G 2V7

( * ) Notice: Subject to any disclaimer, the term of this patent is extended or adjusted under 35 U.S.C. 154(b) by 0 days.

(21) Appl. No.: 10/220,262

(22) PCT Filed: Mar. 7, 2001

(86) PCT No.: PCT/CA01/00283

§ 371 (c)(1),
(2), (4) Date: Jan. 8, 2003

(87) PCT Pub. No.: WO01/66775

PCT Pub. Date: Sep. 13, 2001

(65) Prior Publication Data

US 2003/0162265 A1    Aug. 28, 2003

Related U.S. Application Data

(60) Provisional application No. 60/187,401, filed on Mar. 7, 2000, provisional application No. 60/263,771, filed on Jan. 25, 2001.

(30) Foreign Application Priority Data

Sep. 1, 2000    (CA) .................................... 2317865

(51) Int. Cl.
*C12Q 1/68* (2006.01)
*C12N 15/00* (2006.01)
*C07H 21/04* (2006.01)

(52) U.S. Cl. .................. 435/6; 435/320.1; 536/23.1

(58) Field of Classification Search .................. 435/6, 435/91.2, 320.1; 536/23.1, 24.33; 530/350
See application file for complete search history.

(56) References Cited

U.S. PATENT DOCUMENTS

| 5,017,487 | A |   | 5/1991 | Stunnenberg et al. |
| 5,122,457 | A |   | 6/1992 | Reim et al. |
| 5,135,855 | A |   | 8/1992 | Moss et al. |
| 5,580,759 | A | * | 12/1996 | Yang et al. ............... 435/91.1 |
| 5,773,257 | A |   | 6/1998 | Neilson |
| 5,834,252 | A | * | 11/1998 | Stemmer et al. ........... 435/91.1 |
| 5,976,846 | A |   | 11/1999 | Passmore et al. |
| 6,352,842 | B1 | * | 3/2002 | Short et al. ................ 435/69.1 |

FOREIGN PATENT DOCUMENTS

WO    WO 9916904 A1 *  4/1999

OTHER PUBLICATIONS

Willer et al. Vaccinia virus DNA polymerase promotes DNA pairing and strand-transfer reactions. Virology, vol. 257, pp. 511-523, 1999.*
Zhang et al. DNA strand exchange catalyzed by proteins from Vaccinia virus-infected cells. J Virol., vol. 67, No. 1, pp. 204-212 1993.*
King et al. The joining of blunt DNA ends to 3'-protruding single strands in *Escherichia coli*. Nucleic Acids Res., vol. 26, No. 7, pp. 1749-1754, 1998.*
Tillett et al. Enzyme-free cloning: a rapid method to clone PCR products independent of vector restriction enzyme sites. Nucleic Acids Res., vol. 27, No. 19, p. e26 i-iii, 1999.*
Chuang et al. sinlge-step direct cloning of PCR products. Trends in Genetics, vol. 11, No. 1, pp. 7-8, 1995.*
Aslanidis et al. Ligation-independent cloning of PCR products (LIC-PCR). Nucleic Acids Res., vol. 18, No. 20, pp. 6069-6074, 1990.*
Willer et al. Vaccinia virus DNA polymerase promotes DNA pairing and strand-transfer reactions. Virology, vol. 257, pp. 511-523, 1999.*
Aslanidis et al. Minimal length requirement of the single-stranded tails for ligation-independent cloning (LIC) of PCR products. PCR Methods and Applications, pp. 172-177, 1994.*
Aslanidis et al. Ligation-independent cloning of PCR products (LIC-PCR). Nucleic Acids Res., vol. 18, No. 20, pp. 6069-6074, 1990.*
Acel, A. et al. Efficient gap repair catalyzed in vitro by an intrinsic DNA polymerase activity of human immunodeficientcy virus type 1 integrase. J virol., vol. 72 (3), pp. 2062-2071, 1998.*
Kuijper J. L. et al., "Functional Cloning Vectors for use in Directional CDNA Cloning Using Cohesive Ends Produced with T4 DNA Polymerase". 1992. pp. 147-155. vol. 112, No. 2.
Aslanidis C. et al., "Ligation-Independent Cloning of PCR Products (LIC-PCR)", Nucleic Acids Research. Oct. 25, 1990, pp. 6069-6074, vol. 18, No. 20.
Haun R.S. et al., "Ligation-Independent Cloning of Glutathione S-Transferase Fusion Genes for Expression in *Escherichia-coli*", 1992, pp. 37-43, vol. 112, No. 1.
Tseng H., "DNA Cloning without restriction enzyme and ligase", Biotechniques, Dec. 6, 1999, pp. 1240-1244, vol. 27, No. 6.
Fiorentini P. et al., "Exonuclease I of *Saccharomyces cervisiae* functions in mitotic recombination in vivo and in vitro", Molecular and Cellular Biology, 1997, pp. 2764-2773, vol. 17, No. 5.
Shiraishi H. et al., "A Rapid and Efficient Method for Targeted Random Mutagenesis", 1988, pp. 313-320. vol. 64, No. 2.
Willer D. et al., "Vaccinia virus DNA polymerase promotes DNA pairing and strand-transfer reactions". Virology, May 10, 1999, pp. 511-523, vol. 257, No. 2.
Willer D. et al., "In vitro concatemer formation catalyzed by vaccinia virus DNA polymerase", Virology, Dec. 20, 2000, pp. 562-569, vol. 278, No. 2.

(Continued)

Primary Examiner—Suryaprabha Chunduru
(74) Attorney, Agent, or Firm—Arlir M. Amado; Kramer & Amado, P.C.

(57) ABSTRACT

The present invention provides a method to directionally clone any linear template DNA molecule into any linearized vector. The vector ends may be generated from any restriction enzyme cleavage. The method does not require a ligation step nor the use of carefully controlled conditions as is required with methods involving specific exonucleases alone. It has been determined that specific DNA polymerases are able to efficiently join one or more linear DNA molecules sharing ends with appropriate complementation.

55 Claims, 11 Drawing Sheets

OTHER PUBLICATIONS

Gal J. et al. "Directional cloning of native PCR products with preformed sticky ends (Autosticky PCR*)", Mol. Gen. Genet., 1999, pp. 569-573, vol. 260, No. 6.

Shuldiner A.R. et al, "Ligase-Free Subcloning: A Versatile Method to Subclone Polymerase Chain Reaction (PCR) Product in a Single Day", Analytical Biochemistry, 1991, pp. 9-15, vol. 194, No. 1.

Chuang S.E. et al., "Single-step direct cloning of PCR products", Trends Genet. 1995, pp. 7-8, vol. 11, No. 1.

Shuman S., "Novel Approach to Molecular Cloning and Polynucleotide Synthesis Using Vaccinia DNA Topoisomerase*", The Journal of Biological Chemistry, Dec. 23, 1994, pp. 32678-32684, vol. 269, No. 51.

Wosnick M.A. et al., "Rapid construction of large synthetic genes: total chemical synthesis of two different versions of the bovine prochymosin gene", Gene, 1987, pp. 115-127, vol. 60.

Wosnick M.A. et al., "Total chemical synthesis and expression in *Escherichia coli* of a maize glutathione-transferase (GST) gene", Gene, 1989, pp. 153-16, vol. 76.

Aslanidis, C. et al., "Minimal Length Requirement of the Single-strand Tails for Ligation-independent Cloning (LIC) of PCR Products", PCR Methods and Applications, 1994, pp. 172-177, vol. 4, No. 3.

Tillett D. et al., "Enzyme-free cloning: a rapid method to clone PCR products independent of vector restriction enzyme sites". Nucleic Acids Research. 1999, e26, pp. i-iii, vol. 27, No. 19.

* cited by examiner

SEQUENCE LISTING

<160> NUMBER OF SEQ ID NOS: 11

<210> SEQ ID NO 1
<211> LENGTH: 2958
<212> TYPE: DNA
<213> ORGANISM: Artificial Sequence
<220> FEATURE:
<223> OTHER INFORMATION: pDW101

<400> SEQUENCE: 1

```
ctaaattgta agcgttaata ttttgttaaa attcgcgtta aattttttgtt aaatcagctc      60
atttttttaac caataggccg aaatcggcaa aatcccttat aaatcaaaag aatagaccga    120
gatagggttg agtgttgttc cagtttggaa caagagtcca ctattaaaga acgtggactc    180
caacgtcaaa gggcgaaaaa ccgtctatca gggcgatggc ccactacgtg aaccatcacc    240
ctaatcaagt tttttggggt cgaggtgccg taaagcacta aatcggaacc ctaaagggag    300
cccccgattt agagcttgac ggggaaagcc ggcgaacgtg gcgagaaagg aagggaagaa    360
agcgaaagga gcgggcgcta gggcgctggc aagtgtagcg gtcacgctgc gcgtaaccac    420
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggt ttttcccagt cacgacgttg    600
taaaacgacg gccagtgaat tgtaatacga ctcactatag ggcgaattgg agctccaccg    660
cggtggcggc cgctctagaa ctagtggatc ccccgggctg caggaattcg atatcaagct    720
tatcgatacc gtcgacctcg agggggggcc cggtacccag cttttgttcc ctttagtgag    780
ggttaattgc gcgcttggcg taatcatggt catagctgtt tcctgtgtga aattgttatc    840
cgctcacaat tccacacaac atacgagccg gaagcataaa gtgtaaagcc tggggtgcct    900
aatgagtgag ctaactcaca ttaattgcgt tgcgctcact gcccgctttc cagtcgggaa    960
acctgtcgtg ccagctgcat taatgaatcg gccaacgcgc ggggagaggc ggtttgcgta   1020
ttgggcgctc ttccgcttcc tcgctcactg actcgctgcg ctcggtcgtt cggctgcggc   1080
gagcggtatc agctcactca aaggcggtaa tacggttatc cacagaatca ggggataacg   1140
caggaaagaa catgtgagca aaaggccagc aaaaggccag gaaccgtaaa aaggccgcgt   1200
tgctggcgtt tttccatagg ctccgccccc ctgacgagca tcacaaaaat cgacgctcaa   1260
gtcagaggtg gcgaaacccg acaggactat aaagatacca ggcgtttccc cctggaagct   1320
ccctcgtgcg ctctcctgtt ccgaccctgc cgcttaccgg atacctgtcc gcctttctcc   1380
cttcgggaag cgtggcgctt tctcatagct cacgctgtag gtatctcagt tcggtgtagg   1440
tcgttcgctc caagctgggc tgtgtgcacg aaccccccgt tcagcccgac cgctgcgcct   1500
tatccggtaa ctatcgtctt gagtccaacc cggtaagaca cgacttatcg ccactggcag   1560
cagccactgg taacaggatt agcagagcga ggtatgtagg cggtgctaca gagttcttga   1620
agtggtggcc taactacggc tacactagaa ggacagtatt tggtatctgc gctctgctga   1680
agccagttac cttcggaaaa agagttggta gctcttgatc cggcaaacaa accaccgctg   1740
```

```
gtagcggtgg ttttttttgtt tgcaagcagc agattacgcg cagaaaaaaa ggatctcaag    1800
aagatccttt gatcttttct acggggtctg acgctcagtg aacgaaaac tcacgttaag     1860 ggattttggt catgagatta tcaaaaagga tcttcaccta gatccttta aattaaaaat     1920 gaagttttaa atcaatctaa agtatatatg agtaaacttg gtctgacagt taccaatgct    1980
taatcagtga ggcacctatc tcagcgatct gtctatttcg ttcatccata gttgcctgac    2040
tccccgtcgt gtagataact acgatacggg agggcttacc atctggcccc agtgctgcaa    2100
tgataccgcg agacccacgc tcaccggctc cagatttatc agcaataaac cagccagccg    2160
gaagggccga gcgcagaagt ggtcctgcaa ctttatccgc ctccatccag tctattaatt    2220
gttgccggga agctagagta agtagttcgc cagttaatag tttgcgcaac gttgttgcca    2280
ttgctacagg catcgtggtg tcacgctcgt cgtttggtat ggcttcattc agctccggtt    2340
cccaacgatc aaggcgagtt acatgatccc ccatgttgtg caaaaaagcg gttagctcct    2400
tcggtcctcc gatcgttgtc agaagtaagt tggccgcagt gttatcactc atggttatgg    2460
cagcactgca taattctctt actgtcatgc catccgtaag atgcttttct gtgactggtg    2520
agtactcaac caagtcattc tgagaatagt gtatgcggcg accgagttgc tcttgcccgg    2580
cgtcaatacg ggataatacc gcgccacata gcagaacttt aaaagtgctc atcattggaa    2640
aacgttcttc ggggcgaaaa ctctcaagga tcttaccgct gttgagatcc agttcgatgt    2700
aacccactcg tgcacccaac tgatcttcag catcttttac tttcaccagc gtttctgggt    2760
gagcaaaaac aggaaggcaa aatgccgcaa aaaagggaat aagggcgaca cggaaatgtt    2820
gaatactcat actcttcctt tttcaatatt attgaagcat ttatcagggt tattgtctca    2880
tgagcggata catatttgaa tgtatttaga aaaataaaca ataggggtt ccgcgcacat     2940 ttccccgaaa agtgccac                                                  2958

<210> SEQ ID NO 2
<211> LENGTH: 2958
<212> TYPE: DNA
<213> ORGANISM: Artificial Sequence
<220> FEATURE:
<223> OTHER INFORMATION: pDW101 cut with EcoRI

<400> SEQUENCE: 2
aattcgatat caagcttatc gataccgtcg acctcgaggg ggggcccggt acccagcttt      60
tgttcccttt agtgagggtt aattgcgcgc ttggcgtaat catggtcata gctgtttcct     120
gtgtgaaatt gttatccgct cacaattcca cacaacatac gagccggaag cataaagtgt     180
aaagcctggg gtgcctaatg agtgagctaa ctcacattaa ttgcgttgcg ctcactgccc     240
gctttccagt cgggaaacct gtcgtgccag ctgcattaat gaatcggcca acgcgcgggg    300
agaggcggtt tgcgtattgg gcgctcttcc gcttcctcgc tcactgactc gctgcgctcg    360
gtcgttcggc tgcggcgagc ggtatcagct cactcaaagg cggtaatacg gttatccaca    420
gaatcagggg ataacgcagg aaagaacatg tgagcaaaag gccagcaaaa ggccaggaac    480
cgtaaaaagg ccgcgttgct ggcgtttttc cataggctcc gcccccctga cgagcatcac    540
aaaaatcgac gctcaagtca gaggtggcga aacccgacag gactataaag ataccaggcg    600
tttccccctg gaagctccct cgtgcgctct cctgttccga ccctgccgct taccggatac    660
ctgtccgcct ttctcccttc gggaagcgtg gcgctttctc atagctcacg ctgtaggtat    720
ctcagttcgg tgtaggtcgt tcgctccaag ctgggctgtg tgcacgaacc cccgttcag    780
```

```
cccgaccgct gcgccttatc cggtaactat cgtcttgagt ccaacccggt aagcacgac      840 ttatcgccac tggcagcagc cactggtaac aggattagca gagcgaggta tgtaggcggt      900
gctacagagt tcttgaagtg gtggcctaac tacggctaca ctagaaggac agtatttggt      960
atctgcgctc tgctgaagcc agttaccttc ggaaaaagag ttggtagctc ttgatccggc     1020
aaacaaacca ccgctggtag cggtggtttt tttgtttgca agcagcagat tacgcgcaga     1080 aaaaaggat ctcaagaaga tcctttgatc ttttctacgg ggtctgacgc tcagtggaac     1140
gaaaactcac gttaagggat tttggtcatg agattatcaa aaaggatctt cacctagatc     1200
cttttaaatt aaaaatgaag ttttaaatca atctaaagta tatatgagta aacttggtct     1260
gacagttacc aatgcttaat cagtgaggca cctatctcag cgatctgtct atttcgttca     1320
tccatagttg cctgactccc cgtcgtgtag ataactacga tacggagggg cttaccatct     1380
ggccccagtg ctgcaatgat accgcgagac ccacgctcac cggctccaga tttatcagca     1440 ataaccagc cagccggaag ggccgagcgc agaagtggtc ctgcaacttt atccgcctcc     1500
atccagtcta ttaattgttg ccgggaagct agagtaagta gttcgccagt taatagtttg     1560
cgcaacgttg ttgccattgc tacaggcatc gtggtgtcac gctcgtcgtt tggtatggct     1620
tcattcagct ccggttccca acgatcaagg cgagttacat gatccccat gttgtgcaaa     1680 aaagcggtta gctccttcgg tcctccgatc gttgtcagaa gtaagttggc cgcagtgtta     1740
tcactcatgg ttatggcagc actgcataat tctcttactg tcatgccatc cgtaagatgc     1800
ttttctgtga ctggtgagta ctcaaccaag tcattctgag aatagtgtat gcggcgaccg     1860
agttgctctt gcccggcgtc aatacgggat aataccgcgc cacatagcag aactttaaaa     1920
gtgctcatca ttggaaaacg ttcttcgggg cgaaaactct caaggatctt accgctgttg     1980
agatccagtt cgatgtaacc cactcgtgca cccaactgat cttcagcatc ttttactttc     2040
accagcgttt ctgggtgagc aaaaacagga aggcaaaatg ccgcaaaaaa gggaataagg     2100
gcgacacgga aatgttgaat actcatactc ttcctttttc aatattattg aagcatttat     2160
cagggttatt gtctcatgag cggatacata tttgaatgta tttagaaaaa taaacaaata     2220
ggggttccgc gcacatttcc ccgaaaagtg ccacctaaat tgtaagcgtt aatattttgt     2280
taaaattcgc gttaaatttt tgttaaatca gctcattttt taaccaatag gccgaaatcg     2340
gcaaaatccc ttataaatca aaagaataga ccgagatagg gttgagtgtt gttccagttt     2400
ggaacaagag tccactatta agaacgtgg actccaacgt caagggcga aaaccgtct      2460 atcagggcga tggcccacta cgtgaaccat caccctaatc aagttttttg gggtcgaggt     2520
gccgtaaagc actaaatcgg aaccctaaag ggagccccg atttagagct tgacggggaa     2580
agccggcgaa cgtggcgaga aaggaaggga agaaagcgaa aggagcgggc gctagggcgc     2640
tggcaagtgt agcggtcacg ctgcgcgtaa ccaccacacc cgccgcgctt aatgcgccgc     2700
tacagggcgc gtcccattcg ccattcaggc tgcgcaactg ttgggaaggg cgatcggtgc     2760
gggcctcttc gctattacgc cagctggcga aggggggatg tgctgcaagg cgattaagtt     2820
gggtaacgcc agggttttcc cagtcacgac gttgtaaaac gacggccagt gaattgtaat     2880
acgactcact ataggggcgaa ttggagctcc accgcggtgg cggccgctct agaactagtg     2940
gatcccccgg gctgcagg                                                  2958
```

<210> SEQ ID NO 3
<211> LENGTH: 2958
<212> TYPE: DNA
<213> ORGANISM: Artificial Sequence
<220> FEATURE:
<223> OTHER INFORMATION: pDW101 cut with XhoI

<400> SEQUENCE: 3

```
tcgaggggg gcccggtacc cagcttttgt tcccttagt gagggttaat tgcgcgcttg     60
gcgtaatcat ggtcatagct gtttcctgtg tgaaattgtt atccgctcac aattccacac    120
aacatacgag ccggaagcat aaagtgtaaa gcctggggtg cctaatgagt gagctaactc    180
acattaattg cgttgcgctc actgcccgct ttccagtcgg gaaacctgtc gtgccagctg    240
cattaatgaa tcggccaacg cgcgggaga ggcggtttgc gtattgggcg ctcttccgct    300
tcctcgctca ctgactcgct gcgctcggtc gttcggctgc ggcgagcggt atcagctcac    360
tcaaaggcgg taatacggtt atccacagaa tcaggggata cgcaggaaa gaacatgtga    420
gcaaaaggcc agcaaaaggc caggaaccgt aaaaaggccg cgttgctggc gtttttccat    480
aggctccgcc cccctgacga gcatcacaaa atcgacgct caagtcagag gtggcgaaac    540
ccgacaggac tataaagata ccaggcgttt cccctggaa gctccctcgt gcgctctcct    600
gttccgaccc tgccgcttac cggatacctg tccgccttc tcccttcggg aagcgtggcg    660
ctttctcata gctcacgctg taggtatctc agttcggtgt aggtcgttcg ctccaagctg    720
ggctgtgtgc acgaaccccc cgttcagccc gaccgctgcg ccttatccgg taactatcgt    780
cttgagtcca acccggtaag acacgactta tcgccactgg cagcagccac tggtaacagg    840
attagcagag cgaggtatgt aggcggtgct acagagttct tgaagtggtg gcctaactac    900
ggctacacta agaaggacagt atttggtatc tgcgctctgc tgaagccagt taccttcgga    960
aaaagagttg gtagctcttg atccggcaaa caaaccaccg ctggtagcgg tggttttttt   1020
gtttgcaagc agcagattac gcgcagaaaa aaaggatctc aagaagatcc tttgatcttt   1080
tctacgggt ctgacgctca gtggaacgaa aactcacgtt aagggatttt ggtcatgaga   1140
ttatcaaaaa ggatcttcac ctagatcctt ttaaattaaa aatgaagttt taaatcaatc   1200
taaagtatat atgagtaaac ttggtctgac agttaccaat gcttaatcag tgaggcacct   1260
atctcagcga tctgtctatt tcgttcatcc atagttgcct gactccccgt cgtgtagata   1320
actacgatac gggagggctt accatctggc cccagtgctg caatgatacc gcgagaccca   1380
cgctcaccgg ctccagattt atcagcaata accagccag ccggaagggc cgagcgcaga   1440
agtggtcctg caactttatc cgcctccatc cagtctatta attgttgccg ggaagctaga   1500
gtaagtagtt cgccagttaa tagtttgcgc aacgttgttg ccattgctac aggcatcgtg   1560
gtgtcacgct cgtcgtttgg tatggcttca ttcagctccg gttcccaacg atcaaggcga   1620
gttacatgat cccccatgtt gtgcaaaaaa gcggttagct ccttcggtcc tccgatcgtt   1680
gtcagaagta agttggccgc agtgttatca ctcatggtta tggcagcact gcataattct   1740
cttactgtca tgccatccgt aagatgcttt tctgtgactg gtgagtactc aaccaagtca   1800
ttctgagaat agtgtatgcg gcgaccgagt tgctcttgcc cggcgtcaat acgggataat   1860
accgcgccac atagcagaac tttaaaagtg ctcatcattg gaaaacgttc ttcggggcga   1920
aaactctcaa ggatcttacc gctgttgaga tccagttcga tgtaacccac tcgtgcaccc   1980
aactgatctt cagcatcttt tactttcacc agcgtttctg ggtgagcaaa aacaggaagg   2040
caaaatgccg caaaaaaggg aataagggcg acacggaaat gttgaatact catactcttc   2100
ctttttcaat attattgaag catttatcag ggttattgtc tcatgagcgg atacatattt   2160
gaatgtattt agaaaaataa acaaataggg gttccgcgca catttccccg aaaagtgcca   2220
```

-continued

```
cctaaattgt aagcgttaat attttgttaa aattcgcgtt aaattttgt taaatcagct    2280 cattttttaa ccaataggcc gaaatcggca aaatcccta taaatcaaaa gaatagaccg    2340
agatagggtt gagtgttgtt ccagtttgga acaagagtcc actattaaag aacgtggact    2400
ccaacgtcaa agggcgaaaa accgtctatc agggcgatgg cccactacgt gaaccatcac    2460
cctaatcaag ttttttgggg tcgaggtgcc gtaaagcact aaatcggaac cctaaaggga    2520
gcccccgatt tagagcttga cggggaaagc cggcgaacgt ggcgagaaag gaagggaaga    2580
aagcgaaagg agcgggcgct agggcgctgg caagtgtagc ggtcacgctg cgcgtaacca    2640
ccacacccgc cgcgcttaat gcgccgctac agggcgcgtc ccattcgcca ttcaggctgc    2700
gcaactgttg ggaagggcga tcggtgcggg cctcttcgct attacgccag ctggcgaaag    2760
ggggatgtgc tgcaaggcga ttaagttggg taacgccagg gttttcccag tcacgacgtt    2820
gtaaaacgac ggccagtgaa ttgtaatacg actcactata gggcgaattg gagctccacc    2880
gcggtggcgg ccgctctaga actagtggat cccccgggct gcaggaattc gatatcaagc    2940
ttatcgatac cgtcgacc                                                  2958
```

<210> SEQ ID NO 4
<211> LENGTH: 2958
<212> TYPE: DNA
<213> ORGANISM: Artificial Sequence
<220> FEATURE:
<223> OTHER INFORMATION: pDW101 cut with HindIII

<400> SEQUENCE: 4

```
agcttatcga taccgtcgac ctcgaggggg ggcccggtac ccagcttttg ttcccttag     60 tgagggttaa ttgcgcgctt ggcgtaatca tggtcatagc tgtttcctgt gtgaaattgt    120
tatccgctca caattccaca acatacga gccggaagca taaagtgtaa agcctggggt    180
gcctaatgag tgagctaact cacattaatt gcgttgcgct cactgcccgc tttccagtcg    240
ggaaacctgt cgtgccagct gcattaatga atcggccaac gcgcggggag aggcggtttg    300
cgtattgggc gctcttccgc ttcctcgctc actgactcgc tgcgctcggt cgttcggctg    360
cggcgagcgg tatcagctca ctcaaaggcg gtaatacggt tatccacaga atcaggggat    420
aacgcaggaa agaacatgtg agcaaaaggc cagcaaaagg ccaggaaccg taaaaaggcc    480
gcgttgctgg cgtttttcca taggctccgc cccctgacg agcatcacaa aaatcgacgc    540
tcaagtcaga ggtggcgaaa cccgacagga ctataaagat accaggcgtt tccccctgga    600
agctccctcg tgcgctctcc tgttccgacc ctgccgctta ccggatacct gtccgccttt    660
ctcccttcgg gaagcgtggc gctttctcat agctcacgct gtaggtatct cagttcggtg    720
taggtcgttc gctccaagct gggctgtgtg cacgaacccc ccgttcagcc cgaccgctgc    780
gccttatccg gtaactatcg tcttgagtcc aacccggtaa gacacgactt atcgccactg    840
gcagcagcca ctggtaacag gattagcaga gcgaggtatg taggcggtgc tacagagttc    900
ttgaagtggt ggcctaacta cggctacact agaaggacag tatttggtat ctgcgctctg    960
ctgaagccag ttaccttcgg aaaaagagtt ggtagctctt gatccggcaa acaaaccacc    1020
gctggtagcg gtggtttttt tgtttgcaag cagcagatta cgcgcagaaa aaaaggatct    1080
caagaagatc ctttgatctt ttctacgggg tctgacgctc agtggaacga aaactcacgt    1140
taagggattt tggtcatgag attatcaaaa aggatcttca cctagatcct tttaaattaa    1200
aaatgaagtt ttaaatcaat ctaaagtata tatgagtaaa cttggtctga cagttaccaa    1260
tgcttaatca gtgaggcacc tatctcagcg atctgtctat ttcgttcatc catagttgcc    1320
```

-continued

```
tgactccccg tcgtgtagat aactacgata cgggagggct taccatctgg ccccagtgct    1380
gcaatgatac cgcgagaccc acgctcaccg gctccagatt tatcagcaat aaaccagcca    1440
gccggaaggg ccgagcgcag aagtggtcct gcaactttat ccgcctccat ccagtctatt    1500
aattgttgcc gggaagctag agtaagtagt tcgccagtta atagtttgcg caacgttgtt    1560
gccattgcta caggcatcgt ggtgtcacgc tcgtcgtttg gtatggcttc attcagctcc    1620
ggttcccaac gatcaaggcg agttacatga tcccccatgt tgtgcaaaaa agcggttagc    1680
tccttcggtc ctccgatcgt tgtcagaagt aagttggccg cagtgttatc actcatggtt    1740
atggcagcac tgcataattc tcttactgtc atgccatccg taagatgctt ttctgtgact    1800
ggtgagtact caaccaagtc attctgagaa tagtgtatgc ggcgaccgag ttgctcttgc    1860
ccggcgtcaa tacgggataa taccgcgcca catagcagaa ctttaaaagt gctcatcatt    1920
ggaaaacgtt cttcggggcg aaaactctca aggatcttac cgctgttgag atccagttcg    1980
atgtaaccca ctcgtgcacc caactgatct tcagcatctt ttactttcac cagcgtttct    2040
gggtgagcaa aaacaggaag gcaaaatgcc gcaaaaaagg gaataagggc gacacggaaa    2100
tgttgaatac tcatactctt ccttttttcaa tattattgaa gcatttatca gggttattgt    2160
ctcatgagcg gatacatatt tgaatgtatt tagaaaaata acaaataggg gttccgcgc    2220 acatttcccc gaaaagtgcc acctaaattg taagcgttaa tattttgtta aaattcgcgt    2280 taaattttg ttaaatcagc tcatttttta accaataggc cgaaatcggc aaaatccctt    2340
ataaatcaaa agaatagacc gagatagggt tgagtgttgt tccagtttgg aacaagagtc    2400
cactattaaa gaacgtggac tccaacgtca aagggcgaaa aaccgtctat cagggcgatg    2460
gcccactacg tgaaccatca ccctaatcaa gttttttggg gtcgaggtgc cgtaaagcac    2520
taaatcggaa ccctaagggg agcccccgat ttagagcttg acggggaaag ccggcgaacg    2580
tggcgagaaa ggaagggaag aaagcgaaag gagcgggcgc tagggcgctg gcaagtgtag    2640
cggtcacgct gcgcgtaacc accacacccg ccgcgcttaa tgcgccgcta cagggcgcgt    2700
cccattcgcc attcaggctg cgcaactgtt gggaagggcg atcggtgcgg gcctcttcgc    2760
tattacgcca gctggcgaaa ggggatgtg ctgcaaggcg attaagttgg gtaacgccag    2820
ggttttccca gtcacgacgt tgtaaaacga cggccagtga attgtaatac gactcactat    2880
agggcgaatt ggagctccac cgcggtggcg gccgctctag aactagtgga tccccgggc    2940 tgcaggaatt cgatatca                                                  2958
```

<210> SEQ ID NO 5
<211> LENGTH: 35
<212> TYPE: DNA
<213> ORGANISM: Artificial Sequence
<220> FEATURE:
<223> OTHER INFORMATION: Primer #1

<400> SEQUENCE: 5

```
ttctagagcg gccagaaaca ggcatcttac gcgtg                                35
```

<210> SEQ ID NO 6
<211> LENGTH: 34
<212> TYPE: DNA
<213> ORGANISM: Artificial Sequence
<220> FEATURE:
<223> OTHER INFORMATION: Primer #2

<400> SEQUENCE: 6

-continued

| | |
|---|---|
| tccaccgcgg tggcggccac ggaaacgcct tggt | 34 |

<210> SEQ ID NO 7
<211> LENGTH: 58
<212> TYPE: DNA
<213> ORGANISM: Artificial Sequence
<220> FEATURE:
<223> OTHER INFORMATION: pDW101 was digested with NOtI

<400> SEQUENCE: 7

| | |
|---|---|
| actagttcta gagcggccgc caccgcggtt gatcaagatc tcgccggcgg tggcgcca | 58 |

<210> SEQ ID NO 8
<211> LENGTH: 2502
<212> TYPE: DNA
<213> ORGANISM: Artificial Sequence
<220> FEATURE:
<223> OTHER INFORMATION: pRP406

<400> SEQUENCE: 8

| | |
|---|---|
| tgaccgctac acttgccagc gccctagcgc ccgctccttt cgctttcttc ccttcctttc | 60 |
| tcgccacgtt cgccggcttt ccccgtcaag ctctaaatcg gggctcccct ttagggttcc | 120 |
| gatttagtgc tttacggcac ctcgacccca aaaaacttga ttagggtgat ggttcacgta | 180 |
| gtgggccatc gccctgatag acggtttttc gccctttgac gttggagtcc acgttcttta | 240 |
| atagtggact cttgttccaa actggaacaa cactcaaccc tatctcggtc tattcttttg | 300 |
| atttataagg gattttgccg atttcggcct attggttaaa aaatgagctg atttaacaaa | 360 |
| aatttaacgc gaattttaac aaaatattaa cgcttacaat ttccattcgc cattcaggct | 420 |
| gcgcaactgt tgggaagggc gatcggtgcg ggcctcttcg ctattacgcc agctggcgaa | 480 |
| aggggggatgt gctgcaaggc gattaagttg ggtaacgcca gggttttccc agtcacgacg | 540 |
| ttgtaaaacg acggccagtg ccaagcttat cgatttcgaa cccggggtac cgaatttcat | 600 |
| tttgtttttt tctatgctat aaatagaatt cctcgaggtc gacggtatcg ataagcttga | 660 |
| tatcgaattc ctgcagcccg ggggatccgc attccggtac tgttggtaaa atggaagacg | 720 |
| ccaaaaacat aaagaaaggc ccggcgccat tctatcctct agaggatgga accgctggag | 780 |
| agcaactgca taaggctatg aagagatacg ccctggttcc tggaacaatt gcttttacag | 840 |
| atgcacatat cgaggtgaac atcacgtacg cggaatactt cgaaatgtcc gttcggttgg | 900 |
| cagaagctat gaaacgatat gggctgaata caaatcacag aatcgtcgta tgcagtgaaa | 960 |
| actctcttca attctttatg ccggtgttgg gcgcgttatt tatcggagtt gcagttgcgc | 1020 |
| ccgcgaacga catttataat gaacgtgaat tgctcaacag tatgaacatt tcgcagccta | 1080 |
| ccgtagtgtt tgtttccaaa aaggggttgc aaaaaatttt gaacgtgcaa aaaaaattac | 1140 |
| caataatcca gaaaattatt atcatggatt ctaaaacgga ttaccaggga tttcagtcga | 1200 |
| tgtacacgtt cgtcacatct catctacctc ccggttttaa tgaatacgat tttgtaccag | 1260 |
| agtcctttga tcgtgacaaa acaattgcac tgataatgaa ttcctctgga tctactgggt | 1320 |
| tacctaaggg tgtggccctt ccgcatagaa ctgcctgcgt cagattctcg catgccagag | 1380 |
| atcctatttt tggcaatcaa atcattccgg atactgcgat tttaagtgtt gttccattcc | 1440 |
| atcacggttt tggaatgttt actacactcg gatatttgat atgtggattt cgagtcgtct | 1500 |
| taatgtatag atttgaagaa gagctgtttt tacgatccct tcaggattac aaaattcaaa | 1560 |
| gtgcgttgct agtaccaacc ctattttcat tcttcgccaa aagcactctg attgacaaat | 1620 |
| acgatttatc taatttacac gaaattgctt ctggggggcgc acctctttcg aaagaagtcg | 1680 |

```
gggaagcggt tgcaaaacgc ttccatcttc cagggatacg acaaggatat gggctcactg   1740
agactacatc agctattctg attacacccg aggggggatga taaaccgggc ggggtcggta   1800
aagttgttcc attttttgaa gcgaaggttg tggatctgga taccgggaaa acgctgggcg   1860
ttaatcagag aggcgaatta tgtgtcagag acctatgat tatgtccggt tatgtaaaca    1920
atccggaagc gaccaacgcc ttgattgaca aggatggatg ctacattct ggagacatag    1980 cttactggga cgaagacgaa cacttcttca tagttgaccg cttgaagtct ttaattaaat   2040
acaaaggata tcaggtggcc cccgctgaat tggaatcgat attgttacaa cacccccaaca  2100 tcttcgacgc gggcgtggca ggtcttcccg acgatgacgc cggtgaactt cccgccgccg   2160
ttgttgtttt ggagcacgga aagacgatga cggaaaaaga gatcgtggat tacgtcgcca   2220
gtcaagtaac aaccgcgaaa aagttgcgcg gaggagttgt gtttgtggac gaagtaccga   2280
aaggtcttac cggaaaactc gacgcaagaa aaatcagaga gatcctcata aaggccaaga   2340
agggcggaaa gtccaaattg taaaatgtaa ctgtattcag cgatgacgaa attcttagct   2400
attgtaatcg gatccactag ttctagagcg gccgccaccg cggtggagct ccaattcgcc   2460
ctatagtgag tcgtattgga atcccaggcg acggggcaaa tc                      2502

<210> SEQ ID NO 9
<211> LENGTH: 826
<212> TYPE: DNA
<213> ORGANISM: Artificial Sequence
<220> FEATURE:
<223> OTHER INFORMATION: SFV DNA

<400> SEQUENCE: 9
agaaacaggc atcttacgcg tgtcgattgt tgggaatctt gacaaaacat tccacgtttc    60
catccgaaga atatttccca ctcgtgcgta gcattatgtc catgtacaac acgctgataa   120
aagacgatat tatctggttt aaagagatca ccccgcatct gtacgagtat gtgatgtaca   180
aacaaaacgt gaataacccc tgtttccaaa tttccaccgt agcggtaaat ctatcccgtc   240
atgtacccaa atcttctaca gaacccacca agtatcaaac caagtctaaa caaatgaaaa   300
cgagaatgat tacggacgtt gtatcgttcg acgaaaaatt gaagctcgat gaggcaatta   360
tgtacaaaaa caaaaaggat tatttcgaaa ttaagaaact gtacatgagg ttgaagaaat   420
ttgtacgtaa gaagaaatcg gtaaacgacg gtgtactctg tgacagagtt aaaatgattt   480
acggacacat ccacgagata gaaagagtcg cagtcaatga atacgccatg actaagtcct   540
tgttacatta cgtatttccg aatctgttta cgatgacaa gcatcacctg ttttacagat   600
gcgacaaagt ggatggattg ggggtattat cgtctaagaa actcaatcta atcagagtca   660
tattggaaaa cagattcaaa ataggcaaac aaaaatggac gatgttaaaa agtacatcg    720 acacggtgtg tagcacgggg aaaccgttat tgaagttggg aacgtatccg tattttaaac   780
tgaaaccgtt gaacgccatc gtttccaatt accaaggcgt ttccgt                  826

<210> SEQ ID NO 10
<211> LENGTH: 39
<212> TYPE: DNA
<213> ORGANISM: Artificial Sequence
<220> FEATURE:
<223> OTHER INFORMATION: pRP406 primer

<400> SEQUENCE: 10
ggatctactg ggttaccaga aacaggcatc ttacgcgtg                           39
```

```
<210> SEQ ID NO 11
<211> LENGTH: 35
<212> TYPE: DNA
<213> ORGANISM: Artificial Sequence
<220> FEATURE:
<223> OTHER INFORMATION: pRP406 primer

<400> SEQUENCE: 11
atcctttgta tttaattaaa cggaaacgcc ttggt                              35
```

DNA JOINING METHOD

RELATED RELATIONS

This application is the national phase entry of PCT/CA01/00283 filed Mar. 7, 2001 and claims priority from U.S. Provisional Patent Application No. 60/187,401 filed Mar. 7, 2000, Canadian Patent Application No. 2,317,865 filed Sep. 1, 2000 and U.S. Provisional Patent Application No. 60/263,771 filed Jan. 25, 2001.

FIELD OF THE INVENTION

The present invention is in the field of recombinant DNA technology. Specifically, the present invention relates to a method of directionally joining one or more DNA molecules using a DNA polymerase, and the application of this method to the cloning of PCR products.

BACKGROUND OF THE INVENTION

The Polymerase Chain Reaction (PCR) (Mullis and Faloona 1987; Saiki, Gelfand et al. 1988) is an integral technique in scientific research. Cloning of PCR products is often an obligate step towards reaching a research objective. PCR-cloning presents numerous challenges and various techniques have been devised over the years to minimize its limitations. Cloning of PCR products generally fall into one of the following methodologies; i) traditional PCR-cloning using restriction enzymes and ligase, ii) T-vector or TA-cloning, iii) uracil DNA glycosylase (UDG)-based cloning iv) PCR-based techniques, v) in vivo recombinase methods, and vi) exonuclease-mediated cloning. Each of these methodologies is described below.

i) Traditional PCR-Cloning

Cloning of PCR-amplified DNA was traditionally facilitated by incorporating restriction endonuclease (RE) sites into the PCR primers, allowing for subsequent digestion of the PCR product with the appropriate enzyme followed by insertion into a compatible vector (Sharf et al. 1990). One problem often encountered with this method is that REs are notoriously poor cutters when their recognition sequences are close to the ends of the DNA substrate (Kaufman and Evans 1990). A second complication is that sequences within the PCR-amplified region can be lost if a second restriction site for the same RE is unknowingly present. This necessitates that the complete sequence of the PCR product be known prior to choosing which RE to use. Once the vector and DNA insert have been digested with the same RE, the two DNA molecules can be covalently joined by DNA ligase in a reaction typically taking 4-12 hr. It should be noted that during any ligation reaction, it is critical that the vector and insert are present in appropriate ratios, which is often difficult to determine. The reaction products are then used to transform competent E. Coli cells. A subtle variation on this theme called "ligation by overlap extension" has been devised which does not require any subsequent ligation reaction, but does require two additional primers, and the entire vector sequence itself must be amplified (Shuldiner, Tanner et al. 1991).

Blunt-end cloning of PCR fragments has also been used extensively, although this technique is relatively inefficient because of the problems encountered by DNA ligase when joining together two blunt-ended DNA molecules. This technique is also complicated by the fact that Taq polymerase (the prototypical PCR amplifying enzyme) has a propensity for adding 3' terminal adenine residues through its terminal transferase activity (Clark 1988; Mole, Iggo et al. 1989). Approximately 50% of all PCR products generated using Taq polymerase contain these 3'extensions (Clark, 1988). One way around this problem is to "polish" or remove these added adenine residues with Klenow (Hemsley, Arnheim et al. 1989) or T4 DNA polymerase (Costa and Weiner 1994), adding an additional step to the protocol.

Recent discoveries of different thermostable polymerases including Pfu polymerase from *Pyrococcus furiosis* and $Vent_R$ polymerase from the archaebacteria *Thermococcus litoralis* do not produce 3' adenine residue extensions due to inherent 3'-5' exonuclease activities. In addition to the problems produced by the amplifying polymerase, this technique does not allow for directional cloning, meaning that the orientation of insert in the recombinant DNA cannot be predetermined.

ii) T-Vector and TA-cloning

The terminal transferase activity of Taq polymerase has been exploited by many researchers in a technique now commonly known as TA-cloning. The chosen vector is digested with the appropriate RE so as to yield ends with protruding thymidine residues, the natural complement to the 3'-overhanging adenosine residues found on the PCR-amplified DNA. The most significant drawback of this technique is that vectors must be specifically engineered to produce compatible ends. The only simple way of accomplishing this goal is to restrict the vector to produce blunt ends, and then treat it with Taq polymerase in the presence of only dTTP's. Numerous companies have developed kits based on this technique, including pCR-Script™ SK(S) kit from Stratagene, pGEM®-T from Promega, the SureClone™ ligation kit from Pharmacia and the pT7Blue T-vector kit from Novagen. The main limitation to these methods is that a vector supplied by the manufacturer must be used and a second subcloning step is often necessary to move the cloned DNA fragment into a vector of choice. An inexpensive alternative to buying these kits is to use a T-vector pGEM®-5fZ(+) which is available for little or no cost from the American Type Culture Collection (ATCC). This vector when digested with XcmI provides the T-overhangs used for TA-cloning (Kovalic, Kwak et al. 1991; Mead, Pey et al. 1991). Numerous other T-vectors have been developed independently (Cha, Bishai et al. 1993; Ichihara and Kurosawa 1993) which, after appropriate RE digestion, yield appropriate ends. Such vectors, however, required extensive manipulations to create. Some other potential problems with these kits have been reported recently (Hengen 1995). High backgrounds were observed for the pCR-Script vector when tested alone, PCRII contains a pBR322 origin of replication and thus replicate to low copy numbers, and repeated freeze-thaw cycles at −20° C. can lead to instability and loss of the T-tails. All the T-vector techniques suffer from the drawback that they are non-directional and require a ligation step.

Invitrogen have improved upon traditional TA-cloning by bypassing the need for a ligation step. This method, called TOPO TA-cloning, takes advantage of a reaction catalyzed by a vaccinia virus enzyme called topoisomerase I (Shuman, 1994 and U.S. Pat. No. 5,766,891). Topoisomerase can bind to double-stranded DNA and cleave the phosphodiester backbone in one of the duplex strands. The enzyme is sequence specific, cleaving primarily at the recognition sequence 5'-(C/T)CCTT↓-3' (Shuman and Prescott 1990; Shuman 1991). The enzyme is capable of re-ligating the original strand back together, or ligating two heterologous DNAs in the formation of a recombinant species (Shuman 1992; Shuman 1992). The reaction is very efficient requiring only a 5 minute benchtop incubation. The methodology also has advantages which obviates the need for ligase, does not require knowledge of the entire insert sequence and no additional nucleotides need be added to PCR primers. However, only specific plasmids engineered to contain the TOPO recognition sequence can be used. These vectors are produced by restricting the vector followed by adding specific linkers or adaptors, which is not a trivial task. Another limitation of this technique, is that the TOPO recognition sequence must be located within 10 bp from the 3'-ends of the vector, and furthermore, the insert must have a 5-OH group. The issue has been raised that internal recognition sequences within the amplified DNA may result in complications, however these sites are simply religated and do not impose any restrictions on this technique (Shuman 1994; Stivers, Shuman et al. 1994). Under general use, the Invitrogen kit provided another potential problem (unpublished results). The traditional method for screening clones, called blue-white selection, does not produce definitive results with the Invitrogen kit. Therefore, it is necessary to assay both white and light-blue colonies to ensure the correct construct is obtained.

iii) Uracil DNA-Glycosylase (UDG)-Based Cloning

Rashtchian et al. (1992) developed a ligase independent PCR cloning method using uracil DNA glycosylase (UDG), an enzyme whose normal cellular role is a DNA repair enzyme. The technique requires a 12-bp addition (CUACUACUACUA) to the 5'end of the PCR primers. The glycosylase selectively removes dUMP residues at the ends of the PCR products which disrupts proper base-pairing leading to single-strand 3'-overhangs (Duncan and Chambers 1984; Longo, Berninger et al. 1990). These 3'-overhangs can anneal to appropriately prepared single-strand ends of a vector. Uracil glycosylase is not active with thymine residues, the DNA counterpart of uracil residues (Duncan and Chambers, 1984), and is capable of removing dUMP residues even near the extreme ends (Varshney and van de Sande 1991). This methodology requires that the vector contain the appropriate complementary sequences, and is not amenable to use with proofreading polymerases such as Pfu or Vent$_R$ polymerases (Sakaguchi, Sedlak et al. 1996). The researchers must therefore use Taq polymerase which has a significantly increased error frequency. UDG-based cloning has been commercialized by Life Technologies with their Clone Amp$^R$ pUC system.

A variation on UDG-cloning takes advantage of the abasic sites (AP) produced by UDG-cleavage at dUMP residues. These AP sites are substrates for AP endonucleases such as T4 endonuclease V or human AP endonuclease I. Treatment with either of these repair enzymes yields a 5-P which is suitable for subsequent ligation into the appropriate vector. One drawback of this method is the requirement for a modified base (deoxyuridine) in the primer, and success relies on two enzymes in addition to ligase treatment. A second more obscure variation of UDG-cloning involves the use of a non-base residue called 1,3-propanediol in a predetermined position within the PCR primer, which can yield compatible 5'-ends for cloning, however, this method is much less efficient than other ligase-independent cloning methods (Kaluz and Flint 1994).

iv) PCR-Directed Cloning

PCR-specific cloning methods are often one-step procedures in which the recombinant DNA is produced during the amplification procedure itself. There are many variations on this theme, in which some are ligase-dependent and others are not. These methods are primarily used to produce site-specific mutations in cloned genes. A brief description of the current techniques follows.

Ligase-Dependent Methods a) Stratagene have commercialized a technique for the cloning of blunt-end PCR fragments (Weiner 1993), originally described by Liu and Schwartz (1992). Their methodology requires phosphorylating the 5' end of the PCR primers. The recipient vector is linearized and treated with calf intestinal alkaline phosphatase (CIAP) and then digested with a second restriction enzyme to yield compatible ends. This is a rather convoluted technique but the resultant vector is monophosphorylated and allows for directional cloning. They reported a 95% success rate for directional cloning, however their technique requires an ethanol precipitation and still relies on the actions of ligase.

b) "Hetero-stagger cloning" is another ligase-dependent method which requires a total of four PCR primers (Liu 1996). One set of primers is the traditional PCR primer pair and the second set is equivalent to the first, but includes three additional 5'-GGG residues. The DNA is amplified under normal PCR conditions, the products are denatured by heat and then allowed to reanneal slowly by cooling. Reannealing results in the formation of four distinct species. Only 50% of the products are theoretically cloneable, and only 25% of the products would successfully result in directional clones. The only claimed advantage to this technique is that it allows for modern proofreading polymerases to be used during amplification.

c) A variation of the staggered re-annealing technique has also been used which requires only one primer pair (Ailenberg and Silverman 1996).

d) More recently, Gal et al. (1999) have devised a technique called "autosticky PCR" (AS-PCR) (patent application HU9801320). This technique takes advantage of the observation that abasic sites present in DNA can stall DNA polymerases. In this method, PCR primers are designed to contain abasic sites, which stall the amplifying polymerase, resulting in 5'-overhangs thus enabling ligation into a suitably digested vector. The abasic site is produced by the incorporation of tetrahydrofuran, a stable structural analogue of 2-deoxyribose, at the desired position. This method does provide for directional-cloning, but requires non-traditional reagents and an overnight ligation is recommended.

Ligase-Independent Cloning Methods (LIC)

a) The original ligase PCR-cloning method was described by Shuldiner et al. (1991). Since then, numerous adaptations of this technique have been developed. The technique described here (Temesgen and Eschrich 1996) requires three PCR primers, in which one of the primers contains an additional 24 nucleotides. This process involves two distinct PCR amplifications, thus increasing the probability of introducing PCR errors into the products. However, the linear products can be directly transformed into E. coli obviating the need for ligase. Competent E. coli strain TG2 cells are required, and it is unclear if classical strains such as JM105 or DH5α are able to be substituted. This technique does provide for directional cloning, although the success is related to the PCR parameters in the second PCR step. Any vector can be used in the technique and no restriction enzymes are needed.

b) Garces and Laborda (1995) reported a similar technique only requiring two PCR primers, one of which has a 20 bp 5'-extension. The reaction occurs within a single-tube reaction, and can be adapted for use with any vector, but the efficiency is greatly affected by the PCR parameters.

v) In Vivo Recombination-Based Cloning

PCR-cloning is traditionally completed within the test-tube environment of the laboratory, however, there are at least two reports of cloning using in vivo systems. The following technique was based on the observation that when yeast were co-transfected with a linear template and a gapped plasmid, homologous recombination was able to "patch" the two species together (Guthrie and Fink, 1991). PCR products have since been cloned in yeast using this method (Scharer and Iggo 1992). A similar phenomenon has been reported in *E. coli* (Oliner, Kinzler et al. 1993). This technique presumably takes advantage of endogenous exonuclease or polymerase activities encoded by the host, but there is no speculation as to what is exactly occurring. The PCR primers are designed to contain 5'-sequences which are identical to sequences adjacent to a chosen RE site. The linearized vector and the PCR products are co-transfected into *E. coli* strain JC8679. This technique may not be suitable for use with traditional *E. coli* strains because independent reports indicate that DH5α cells cannot catalyze intramolecular gap repair, and thus might not be expected to catalyze inter-molecular recombination (Hanahan, 1985). A similar methodology described by Bubeck et al. (1993) reported successful recombination in DH5α cells but only if they were transformed by $CaCl_2$ methods. Two more commonly used techniques for bacterial transformation known as heat shock and electroporation were unsuccessfully used in the above experiment.

vi) Exonuclease-Based PCR Cloning

A completely different approach to the cloning of PCR fragments involves the generation of single-strand overhangs through the action of various exonucleases. All of the exo-based methods are ligase-independent and are based on the technique originally reported by Aslanidis and deJong, (1990). Numerous modifications to this technique have allowed for improvements in the method (Haun, Serventi et al. 1992; Kuijper, Wiren et al. 1992), both of which use the 3'-5' exonuclease activity of T4 DNA polymerase. PCR primers are designed to contain a 5'-extension complementary to sequences adjacent to a chosen RE site within the vector. Single-strand overhangs are generated through the exonucleolytic digestion by T4 pol and annealing of single-strand regions between the vector and insert is sufficiently stable to allow for direct bacterial transformation. These techniques require delicate control of incubation periods, as these enzymes are extremely efficient, and if one is not careful, excess DNA can be digested. Kuijper et al. (1992) also reported that there is great variation between enzyme preparations, therefore, requiring fine-tuning of temporal conditions with each new batch of enzyme. A second drawback to these specific methods is the requirement for the addition of dTTPs or dATPs in the exo reaction to stop the enzyme at the appropriate positions.

A similar method to that reported above uses a different enzyme called exonuclease III (Hsiao 1993), which was originally used for cloning in 1992 (Kaluz, Kolble et al. 1992). Its limitation is that only blunt-ended or 5'-overhanging substrates can be efficiently cloned. Substrates with 3'-overhangs cannot be cloned by this method.

More recently, phage T7 Gene6 exonuclease has been used for PCR-cloning (Zhou and Hatahet 1995). In this technique PCR primers are designed to include internal phophorothioate bonds positioned towards the center of the primers. The 3'end of the primers are standard PCR primers, whereas the 5' ends are designed to be complementary to sequences adjacent to a certain RE site. This method produces directional clones and is ligase-independent but requires the use of non-standard PCR primers. U.S. Pat. No. 5,580,759 (Yang, et al. also discloses a method of construction of recombinant DNA by exonuclease recession.

In summary, a wide variety of methods exist for the cloning of PCR products, and each has its advantages and disadvantages. There remains a need for an optimal cloning method having the following characteristics:

compatible with the use of any vector and any restriction enzyme;
requires only two PCR primers comprised solely of natural bases;
ligase independent;
time efficient;
provides almost exclusively directional cloning;
only the terminal sequences of the amplified region need to be known;
no possibility of internal digestion of the PCR product;
any type of amplifying polymerase can be used;
compatible with various readily available *E. coli* strains;
transformation of bacteria can be accomplished through a variety of techniques;
unambiguous selection; and
adaptable to other techniques such as combinatorial cloning.

SUMMARY OF THE INVENTION

The present inventors have determined that DNA polymerase, such as vaccinia DNA polymerase, is able to efficiently join one or more linear DNA molecules. The method uses recombination between sequence elements present at the end(s) of a series of DNA molecules to specify the junctions and uses specific DNA polymerases to join the molecules. The method may be used to join one or more linear DNA molecules precisely in a single procedure. The primary application of this new method is in the construction of recombinant DNA molecules, as specifically applied to the cloning of PCR products into any desired vector. The present method offers all of the characteristics of an optimal cloning method listed above.

Accordingly, the present invention provides a method of joining two linear DNA molecules comprising the step of:
providing a first linear DNA molecule having a first end and a second end;
providing a second linear DNA molecule having a first end and a second end;
wherein the first linear DNA molecule has a sequence of nucleotides at either the first end or the second end that is complementary to a sequence of nucleotides at either the first end or the second end of the second linear DNA molecule and
incubating the two linear DNA molecules in the presence of a DNA polymerase under conditions whereby the two linear DNA molecules are joined.

In one embodiment, the present invention provides a method of joining two or more linear DNA molecules comprising the steps of:
providing two or more linear DNA molecules, each having an x and x' strand, having opposite polarities, wherein the 5' end of the x' strand of one linear DNA molecule has a sequence of nucleotides that is complementary to the 5' end of the x strand of another linear DNA molecule to which it is to be joined; and
incubating the two or more linear DNA molecules in the presence of a DNA polymerase under conditions whereby the two or more linear DNA molecules are joined;

wherein the DNA polymerase has intrinsic exonuclease activity and is capable of performing the DNA joining reaction of the invention.

This method may be used to join any number of DNA molecules. The key is to ensure that the molecules are selected such that the ends of each DNA molecule have complementary regions to the molecule it is to be joined to. Internal molecules must have complementary regions on both ends. Particular applications of this technology are the combinatorial fusion of DNA cassettes and preparation of synthetic genes. The technique is also useful for reconstruction of fragmented clones.

The method of the invention may also be applied to the recircularization of single DNA molecules in which the ends bear substantially complementary nucleic acid sequences. Application of this technique may be in the area of site-directed mutagenesis.

The DNA polymerases that may be used in the method of the invention include all DNA polymerases having intrinsic exonuclease activity, preferably 3'-5' exonuclease activity, that are capable of performing the DNA joining reaction of the invention. Such a polymerase may be identified by assaying for its ability to join two linear DNA molecules, having ends with complementary nucleotide sequences, as described herein. Preferably the DNA polymerase is selected from the group consisting of vaccinia virus DNA polymerase, T4 DNA polymerase and the Klenow fragment of E. coli DNA polymerase I. Most preferably, the DNA polymerase is vaccinia virus DNA polymerase. The length of the complementary nucleotide sequence on each linear DNA molecule may be between about 5 and about 100 nucleotides, preferably between about 8 and about 50 nucleotides and, most preferably, between about 10 and 35 nucleotides. Various, well known stimulatory factors may be added to the incubation mixture. Such stimulatory factors are those that increase the efficiency of the reaction and stabilize the desired reaction products, for example, single strand DNA binding proteins.

In another of its embodiments, the present invention involves a method of constructing a recombinant:DNA molecule comprising the steps of:
providing a linearized vector DNA molecule and a template DNA molecule, each having a first and a second end;
providing a first primer DNA molecule having a 5' end that comprises nucleotide sequences that will incorporate nucleotide sequences that are complementary to the first end of the linearized vector molecule onto the first end of the template DNA molecule and a 3' end that is designed to hybridize to a suitable location on the first end of the template DNA molecule;
providing a second primer DNA molecule having a 5' end that comprises nucleotide sequences that will incorporate nucleotide sequences that are complementary to the second end of the linearized vector molecule onto the second end of the template DNA molecule and a 3' end that is designed to hybridize to a suitable location on the second end of the template DNA molecule;
amplifying the template DNA molecule using the polymerase chain reaction with the first and second primers to generate a PCR amplified product; and
incubating the PCR amplified product with the linearized vector DNA molecule in the presence of a DNA polymerase to generate a recombinant DNA molecule;
wherein the DNA polymerase has intrinsic exonuclease activity and is capable of performing the DNA joining reaction of the invention.

The DNA polymerases that may be used in the method of the invention include all DNA polymerases having intrinsic exonuclease activity, preferably 3'-5' exonuclease activity, that are capable of performing the DNA joining reaction of the invention. Such polymerases may be identified by assaying for the ability to join two linear DNA molecules having ends with complementary nucleotide sequences, as described herein. Preferably the DNA polymerase is selected from the group consisting of vaccinia virus DNA polymerase, T4 DNA polymerase and the Klenow fragment of E. coli DNA polymerase I. Most preferably, the DNA polymerase is vaccinia virus DNA polymerase. Various, well known stimulatory factors may be added to the incubation mixture. Such stimulatory factors are those that increase the efficiency of the reaction and stabilize the desired reaction products, for example, single strand DNA binding proteins.

The number of complementary nucleotides that are incorporated onto the first and second ends of the template DNA molecule may be between about 5 and about 100 nucleotides, preferably between about 8 and about 50 nucleotides and, most preferably, between about 10 and 35 nucleotides.

This method could be readily applied to the insertion of two or more DNA molecules into a vector. Each additional molecule would require two further bipartite PCR primers, each having a first portion that primes a PCR extension that is complementary to the appropriate end of the adjacent molecule and a second portion that is complementary to the appropriate end of the DNA molecule to be amplified.

The linear DNA molecule to be inserted into a linearized vector using the method of the invention need not be obtained through PCR amplification. Therefore the present invention further involves a method of constructing a recombinant DNA molecule comprising:
providing a linearized vector DNA molecule;
providing a linear insert DNA molecule having ends that are substantially complementary to the ends of the linearized vector DNA molecule to which they are to be joined; and
incubating the linearized vector DNA molecule and linear insert DNA molecule in the presence of a DNA polymerase under conditions where the two DNA molecules are joined;
wherein the DNA polymerase has intrinsic exonuclease activity and joins the DNA molecules. The linear insert DNA molecule may be obtained by any known means, for example, chemical synthesis, ligation or annealing.

The present invention provides a method to directionally clone any template DNA molecule into a single restriction site of any vector. The vector ends may be generated from any restriction enzyme cleavage. The method does not require a ligation step nor the use of carefully controlled conditions as is required with methods involving specific exonucleases alone.

The present invention is also directed to kits containing reagents for conducting the method.

These and other aspects of the present invention will be described in greater detail hereinbelow.

BRIEF DESCRIPTION OF THE DRAWINGS

The features of the present invention will become more apparent from the following description in which reference is made to the appended drawings in which.

DETAILED DESCRIPTION OF THE INVENTION

Definitions

Figure 1:
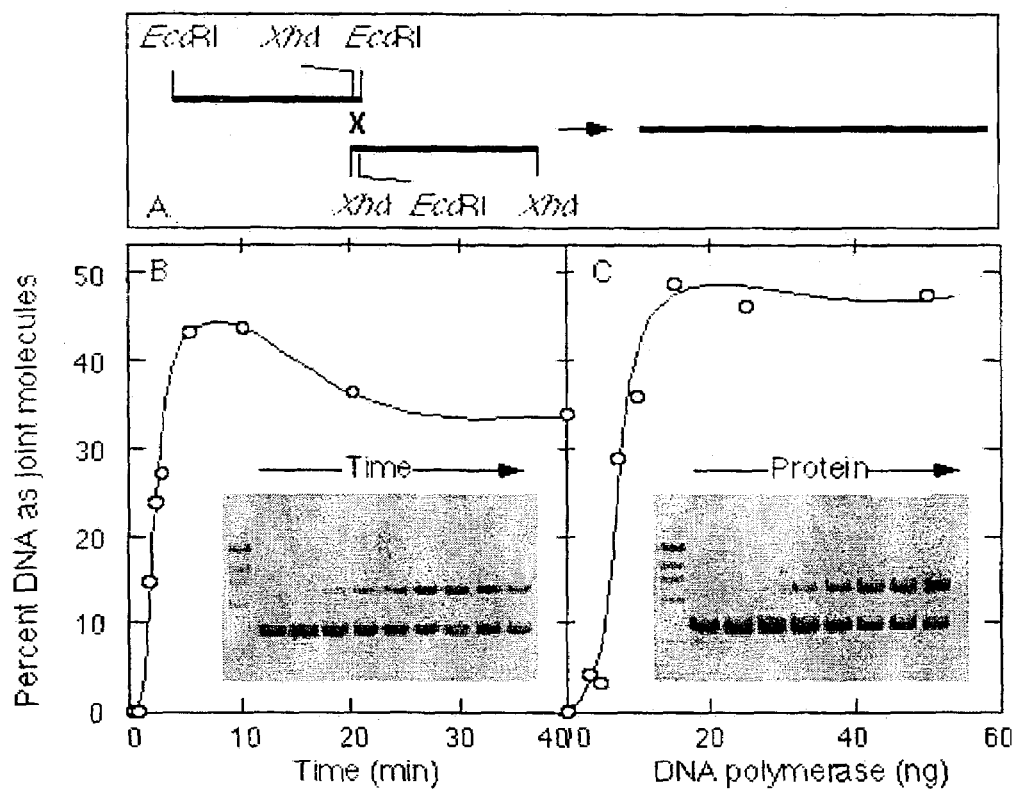
FIG. 1 shows a schematic representation (Panel A) and the experimental results (Panels B and C) for the joining of two linear DNA molecules using the method of the invention.

The term "complementary" as used herein, refers to nucleotide sequences in a single stranded molecule of DNA that are sufficiently complementary to a strand of nucleotide sequences in another DNA molecule to specifically (non-randomly) hybridize to it with consequent hydrogen bonding.

The term "linear DNA molecule" as used herein refers to a double stranded (duplex) nucleic acid molecule comprising two strands of opposite polarity (sense and antisense) of substantially complementary polynucleotides held together by one or more hydrogen bonds between each of the complementary bases present in a base pair of the molecule.

The term "recombinant DNA molecule" as used herein refers to a hybrid DNA molecule comprising at least two nucleotide sequences not normally found together in nature.

The term "nucleotide" as used herein refers to a monomeric unit of DNA consisting of a sugar moiety (pentose), a phosphate group and a nitrogenous heterocyclic base. The base is linked to the sugar moiety via the glycosidic carbon (1' carbon of pentose) and that combination of base and sugar is a nucleoside. When the nucleoside contains a phosphate group bonded to the 3' or 5' position of the pentose it is referred to as a nucleotide. A sequence of operatively linked nucleotides is typically referred to herein as a "nucleotide sequence", and their grammatical equivalents, and is represented by a formula whose left to right orientation is in the conventional direction of 5'-terminus to 3'-terminus.

DNA Joining Methods

The present invention relates to a method to join two or more linear DNA molecules using specific DNA polymerases. The method relies on the ability of specific DNA polymerases to facilitate the recombination of linear DNA molecules having ends that share complementary nucleotides.

Accordingly, the present invention provides a method of joining two linear DNA molecules comprising the step of:
providing a first linear DNA molecule having a first end and a second end;
providing a second linear DNA molecule having a first end and a second end,
wherein the first DNA molecule has a sequence of nucleotides at either the first end or the second end that is complementary to a sequence of nucleotides at either the first end or the second end of the second linear DNA molecule; and
incubating the two linear DNA molecules in the presence of a DNA polymerase under conditions whereby the two linear DNA molecules are joined.

The first and/or second linear DNA molecule can be comprised of one or more linear DNA molecules. For example, the first linear DNA molecule may consist of two linear DNA molecules that have been previously joined using the method of the invention.

In one embodiment, the present invention provides a method of joining two or more linear DNA molecules comprising the steps of:
providing two or more linear DNA molecules, each having an x and x' strand having opposite polarities, wherein the 5' end of the x' strand of each linear DNA molecule has a sequence of nucleotides that is complementary to a sequence of nucleotides at the 5' end of the x strand of the linear DNA molecule to which it is to be joined; and
incubating the two or more linear DNA molecules in the presence of a DNA polymerase under conditions whereby the two or more linear DNA molecules are joined;
wherein the DNA polymerase has intrinsic exonuclease activity and is capable of performing the DNA joining reaction of the invention.

DNA polymerases that work in the methods of the invention are those having intrinsic exonuclease activity, preferably 3'-5' exonuclease activity, that are capable of performing the DNA joining reaction of the invention. Such polymerases may be identified by assaying for the ability to join two linear DNA molecules having ends with complementary nucleotide sequences as described in Experiment 2 herein (Experimental Section). Purified vaccinia DNA polymerase was used in the examples presented herein. The reaction has also been shown to work with T4 DNA polymerase and the Klenow fragment of E. coli DNA polymerase I. The DNA polymerases of the invention are either commercially available or may be prepared using standard recombinant DNA technology. For example, vaccinia DNA polymerase may be purified from vaccinia-infected BSC-40 cells as described in McDonald and Traktman (1994) and Willer, Mann et al. (1999). Alternatively, vaccinia DNA polymerase may be purified from cells infected with wild-type vaccinia virus. We assay polymerases to measure their ability to join two linear DNA molecules having ends with complementary nucleotide sequences. These include but are not limited to, those encoded by bacteriophage (e.g. T4, T7), bacteria (e.g. E. coli), fungi (e.g. S. cerevisiae) and viruses (e.g. poxviruses, herpes viruses, adenoviruses, African swine fever virus and other Iridoviruses, and Bacculoviruses). The DNA polymerases useful in the invention preferably have intrinsic 3'-5' exonuclease activity. The invention also extends to cover those DNA polymerases with 5'-3' exonuclease activity.

Various known stimulatory factors may be added to the incubation mixture to enhance the efficiency of the reaction and/or stabilize the reaction products. Suitable stimulatory factors include single strand DNA binding proteins. Some single strand DNA binding proteins that may be used include, but are not limited to, vaccinia and *E. coli* single strand binding proteins, Herpes simplex virus ICP8 protein and yeast and human replication Protein A (eg. yRPA and hRPA). A skilled person would be able to readily identify other suitable stimulatory factors that may be usefully combined with a DNA polymerase in the methods of the invention. In one aspect of the invention, the vaccinia single strand binding protein is used to enhance the yield of a DNA joining reaction employing vaccinia DNA polymerase.

The degree of complementation between the ends of the linear DNA molecules can vary from between about 5 and about 100 nucleotides, preferably between about 8 and about 50 nucleotides and, most preferably, between about 10 and 35 nucleotides. The linear DNA molecules that may be joined using the method of the invention may be obtained from genomic DNA of prokaryotic or eukaryotic genomes, as well as from various vectors, including plasmids, cosmids, phage, BACs and the like, using restriction enzyme cleavage. Alternatively, the linear DNA molecule may be synthesized by chemical techniques, for example, using automated synthesis and the like. The DNA molecule may also be derived from RNA species, such as mRNA, tRNA and rRNA, from any species and may first be converted to cDNA by reverse transcriptase and the amplified as described in Sambrook et al. (1989).

In its most general application, the present invention provides a method to join two or more linear DNA molecules. FIG. 1 shows a schematic of this reaction for the joining of two linear DNA molecules (Panel A). This illustrates how two substrates sharing complementary sequences on the left and right ends can be incubated in the presence of a specific DNA polymerase to form a dimer. Panel C of FIG. 1 shows the results from an experiment where a 1:1 mixture of two substrates, sharing 35 bp of complementary sequence at the left and right ends, was incubated with varying quantities of vaccinia DNA polymerase and the products separated by size using an agarose gel. No reaction is observed when the polymerase is omitted (lane 2) and increasing yields of products were seen when increasing amounts of polymerase were added (lanes 3-9).

Figure 2:
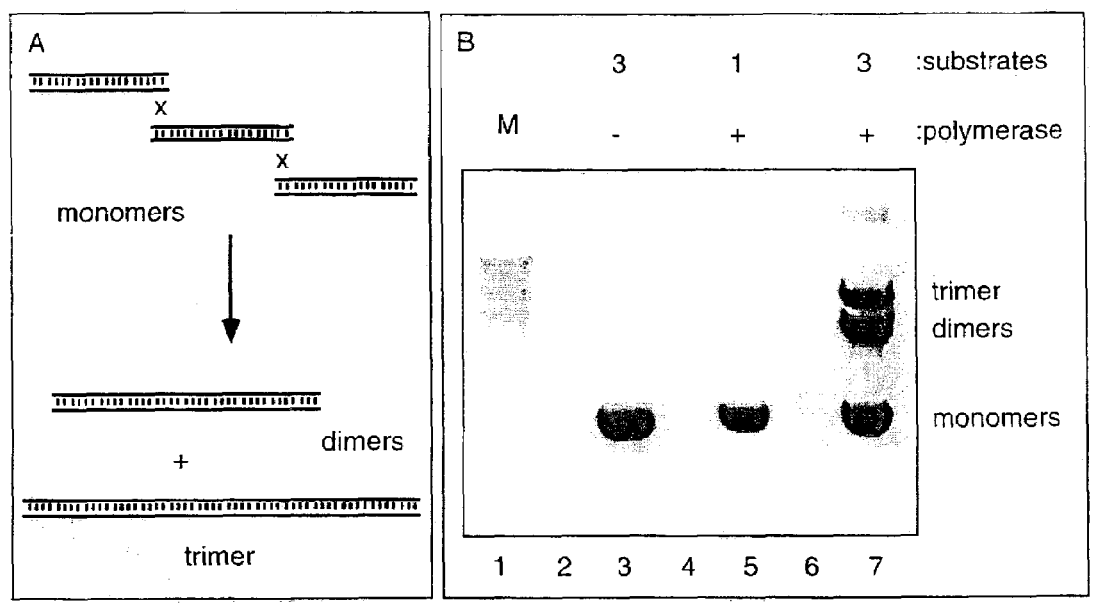
FIG. 2 shows a schematic representation (Panel A) and the experimental results (Panel B) for the joining of three linear DNA molecules using the method of the invention.

FIG. 2, Panel A, shows the joining of three linear DNA molecules to produce a trimer. In this case the "middle" molecule must have sequences of DNA on each end that are complementary to the ends of the two flanking molecules. The results from an actual experiment where the middle molecule had about 20 bp of complementary DNA sequences with the two flanking molecules on each end are shown in Panel B of FIG. 2. The results in Panel B of FIG. 2 also illustrate an important control (lane 5). The polymerase will not form concatemers when provided with just one of the three substrates, since the ends of identical molecules do not share the appropriate type of complementation. This specificity means that one can direct exactly how two or more molecules are fused, simply by controlling a nearly infinite array of terminal sequence overlaps.

Accordingly, the present invention provides a method of joining three linear DNA molecules comprising:

providing a first DNA molecule having a first end and a second end;

providing a second linear DNA molecule having a first end and a second end;

providing a third linear DNA molecule having a first end and a second end;

wherein the first linear DNA molecule has a sequence of nucleotides at the first end that is complementary to a sequence of nucleotides at either the first or the second end of the second linear DNA molecule and wherein the first linear DNA molecule has a sequence of nucleotides at the second end that is complementay to a sequence of nucleotides at either the first or the second end of the third linear DNA molecule, and incubating the three linear DNA molecules in the presence of a DNA polymerase under conditions whereby the three linear DNA molecules are joined.

One skilled in the art will appreciate that the above method can be used to join any number of DNA molecules provided the DNA molecules contain the appropriate complementary sequences to join one molecule to another. For example, to join a fourth DNA molecule to the three DNA molecules described above, either the second or third DNA molecule will have a sequence of nucleotides at its free end (i.e. the end that is not joined to the first DNA molecule) that is complementary to a sequence on one end of the fourth DNA molecule.

Figure 3:
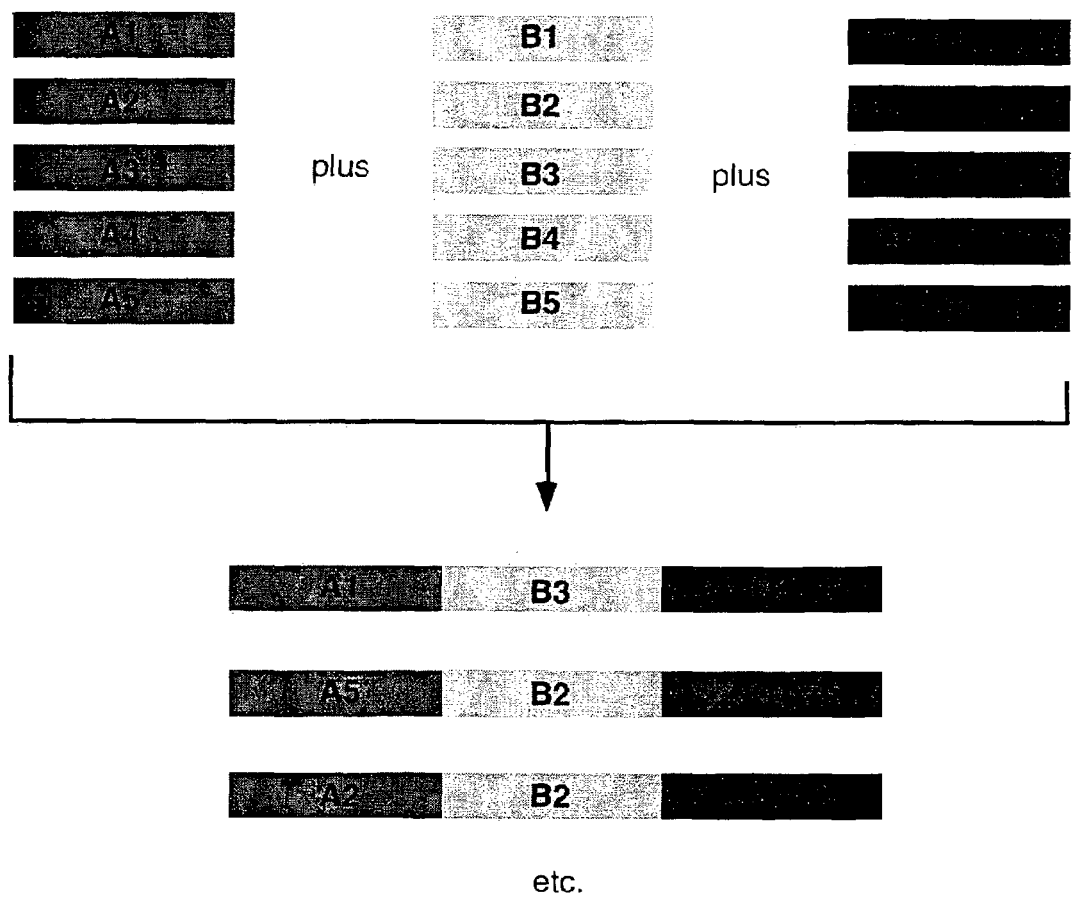
FIG. 3 shows a schematic representation of the application of the method of the invention to the combinatorial fusion of DNA cassettes.

Another application of the present invention is in the combinatorial fusion of DNA cassettes as illustrated in FIG. 3. In this example, three different pools of DNA molecules are prepared. Within a pool of molecules, the central portion of each molecule varies in sequence while the ends are identical. For example, as shown in FIG. 3, A1-A5 all have the same about 5 to about 100, preferably about 8 to about 50, more preferably about 10 to about 35, nucleotide sequences at the right end, but the remaining portion of the molecules vary in sequence. The left ends of the molecules in the "B" pool are compatible with the right ends of molecules in the "A" pool. Similarly, the left ends of the molecules in the "C" pool are compatible with the right ends of molecules in the "B" pool. By compatible, it is meant that they share appropriate complementary sequences ranging from about 5 to about 100, preferably about 8 to about 50, more preferably about 10 to about 35, nucleotides. Incubation of the mixture of molecules from pools A, B and C with a DNA polymerase useful in the method of the invention will create trimers composed of one of each of the molecules selected from the A, B, and C pools. The resulting pool of trimers should express a random assortment of "A", "B" and "C" variants. The number of "pools" and molecules within each pool could be varied to potentially produce a random assortment of millions of different DNA molecules. The combinatorial fusion of DNA cassettes using the method of the invention may be applied to the construction of DNA sequences encoding novel proteins through the combinatorial fusion of DNA molecules encoding different protein structural domains. These libraries of proteins may be screened for novel binding specificities.

The method of the invention may also be used to recombine (circularize) a single DNA molecule in which the ends bear substantially complementary nucleic acid sequences. Therefore, the present invention also relates to a method of circularizing linear DNA molecules comprising:

PCR amplifying a linear DNA molecule in the presence of primers that will introduce substantially complementary nucleic acid sequences onto each end of the linear DNA molecule; and incubating the PCR amplified linear DNA molecule in the presence of a DNA polymerase under conditions where the linear DNA molecule is circularized;

wherein the DNA polymerase has intrinsic exonuclease activity and circularizes the DNA molecule.

One use for the application of the method of the invention to the circularization of single DNA molecules is in the area of site directed mutagenesis. For example, a plasmid comprising a gene of interest could be PCR amplified using primers designed to incorporate substantially complementary nucleic acid sequences on each end. If one designed the primers so that mutations are introduced into the plasmid within the gene of interest, mutated forms of the gene may be obtained.

Several additional reaction features were investigated. Perhaps most important is the fact that vaccinia polymerase does not seem to care what type of ends are present on the two recombining molecules. Molecules bearing 5' overhanging, 3' overhanging or blunt ends, in any pairwise combination, were still substrates as long as the two molecules shared appropriate sequence complementation.

DNA Cloning Methods

In another of its embodiments, the present invention provides a method of cloning any double stranded PCR product into any vector. Therefore there is provided, a method of constructing a recombinant DNA molecule comprising the steps of:
  providing a linearized vector DNA molecule and a template DNA molecule, each having a first and a second end;
  providing a first primer DNA molecule having a 5' end that comprises nucleotide sequences that will incorporate nucleotide sequences that are complementary to the first end of the linearized vector molecule onto the first end of the template DNA molecule and a 3' end that is designed to hybridize to a suitable location on the first end of the template DNA molecule;
  providing a second primer DNA molecule having a 5' end that comprises nucleotide sequences that will incorporate nucleotide sequences that are complementary to the second end of the linearized vector molecule onto the second end of the template DNA molecule and a 3' end that is designed to hybridize to a suitable location on the second end of the template DNA molecule;
  amplifying the template DNA molecule using the polymerase chain reaction with the first and second primers to provide a PCR amplified product; and
  incubating the PCR amplified product with the linearized vector DNA molecule in the presence of a DNA polymerase to generate a recombinant DNA molecule;
  wherein the DNA polymerase has intrinsic exonuclease activity and is capable of performing the DNA joining reaction of the invention.

Figure 4:
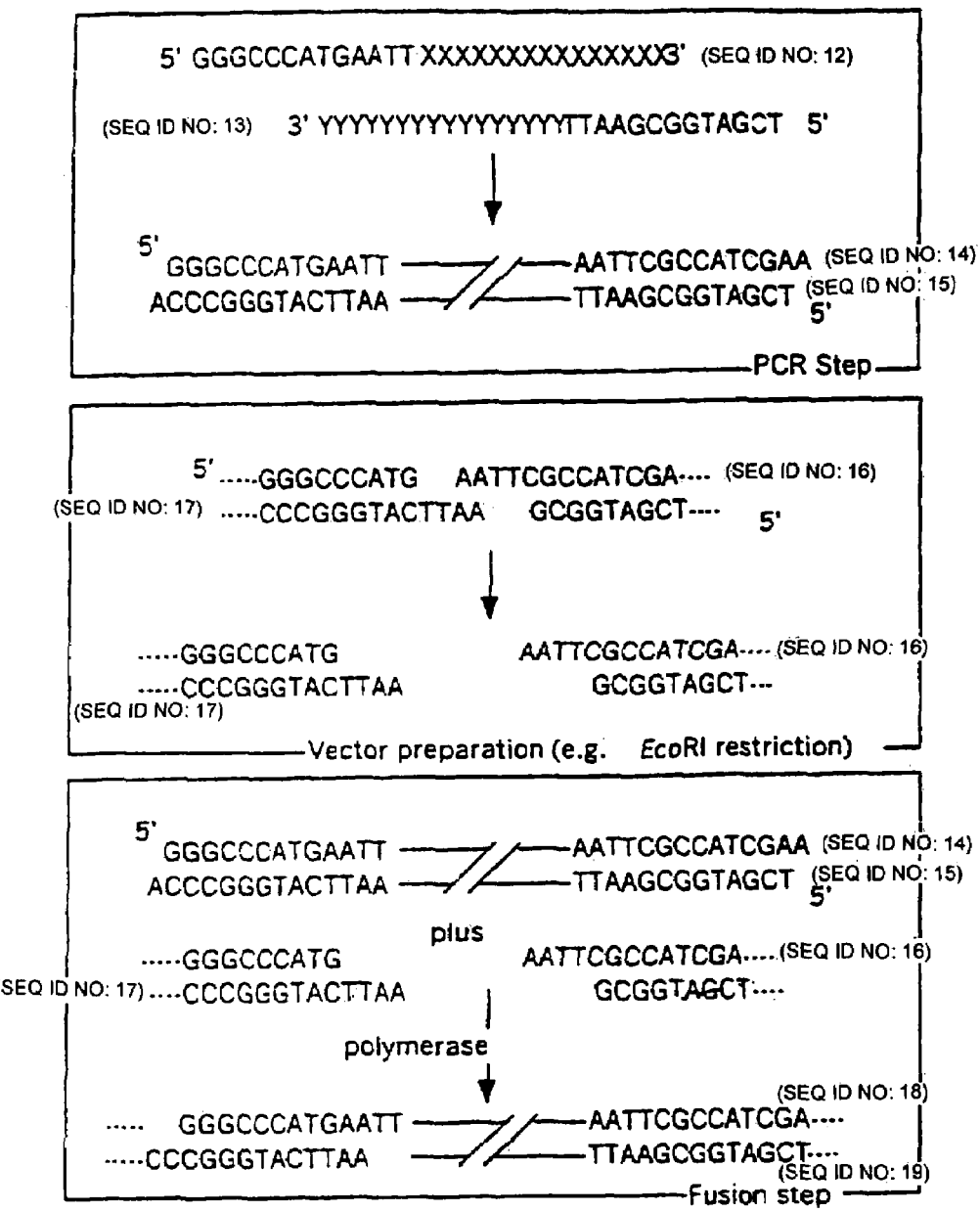
FIG. 4 is a schematic showing the application of the method of the invention to the cloning of PCR products.

In this method, all that is required is that the PCR primers be extended to incorporate some nucleotides that duplicate the base sequence flanking the chosen cloning site in the vector. The suggested approach is illustrated in FIG. 4. A set of two bipartite primers is designed. The 3' end of the first primer molecule is designed to hybridize with the first end of the template DNA molecule, and the 5' end of the first primer molecule has a sequence of from about 5 to about 100, preferably about 8 to about 50, more preferably about 10 to about 35, nucleotides that are designed to incorporate sequences in the final PCR product that are complementary to the first end of the vector DNA molecule. The 3' end of the second primer is designed to hybridize with the second end of the template DNA molecule, and the 5' end of the second primer molecule has a sequence of from about 5 to about 100, preferably about 8 to about 50, more preferably about 10 to about 35, nucleotides that are designed to incorporate sequences in the final PCR product that are complementary to the second end of the vector DNA molecule. The two primers are then annealed to the template DNA molecule which is then PCR amplified using standard conditions to generate a PCR amplified product. The vector is prepared by treating it with the appropriate restriction enzyme to cut it at the chosen insert site using standard conditions.

The term primer as used herein is meant to describe a bipartite primer or a primer having a first and second portion. A first portion of the primer is designed to be complementary to the appropriate end of a template DNA molecule and a second portion of the primer is designed to be complementary to nucleotide sequences on one side of the chosen restriction site of the vector. The bipartite oligonucleotide primers of the present invention may be broadly defined as single stranded oligonucleotides that are complementary to DNA molecules of interest and will allow the DNA molecules to be incorporated into a vector. Bipartite primers will generally have a minimum length of about 18 nucleotides and a maximum length of about 200 nucleotides, preferably about from 25 nucleotides to about 100 nucleotides, more preferably from about 30 nucleotides and about 40 nucleotides. This method could be readily applied to the insertion of two or more DNA molecules into a vector. Each additional molecule would require two further bipartite PCR primers, each having a first portion that primes a PCR extension that is complementary to the appropriate end of the adjacent molecule and a second portion that is complementary to the appropriate end of the DNA molecule to be amplified.

The PCR amplified product and the linearized vector are then incubated in a suitable reaction buffer in the presence of a DNA polymerase having intrinsic exonuclease activity, preferably 3'-5' exonuclease activity, that is capable of performing the DNA joining reaction of the invention, for about 5 to about 60 minutes, preferably from about 10 to about 40 minutes, most preferably from about 15 to about 30 minutes. Purified vaccinia DNA polymerase was used in the examples presented herein. The reaction has also been shown to work with T4 DNA polymerase and the Klenow fragment of E. Coli DNA polymerase I. The reaction buffer may be any buffer that is used in DNA annealing reactions. The temperature may be in the range of from about 35-40° C, more preferably about 37° C.

The DNA polymerases that work in this method may be identified by assaying for the ability to join two linear DNA molecules having ends with appropriate complementary sequences as describe in Example 2 herein (Experimental Section). The DNA polymerases of the invention are either commercially available or may be prepared using standard recombinant DNA technology. For example, vaccinia DNA polymerase may be purified from vaccinia-infected BSC-40 cells as described in McDonald and Traktman (1994) and Willer, Mann et al. (1999). Alternatively, vaccinia DNA polymerase may be purified from cells infected with wild-type vaccinia virus. We assay polymerases to measure their ability to join two linear DNA molecules having ends with complementary nucleotide sequences. These include, but are not limited to, those encoded by bacteriophage (e.g. T4, T7), bacteria (e.g. E. coli), fungi (e.g. S. cerevisiae) and viruses (e.g. poxviruses, herpes viruses, adenoviruses, African swine fever virus and other Iridoviruses, and Bacculoviruses). The DNA polymerases useful in the invention preferably have intrinsic 3'-5' exonulcease activity. The invention also extends to cover those DNA polymerases with 5'-3' exonulcease activity.

Various known stimulatory factors may be added to the incubation mixture to enhance the efficiency of the reaction and/or stabilize the reaction products. Suitable stimulatory factors include single strand DNA binding proteins. Some single strand DNA-binding proteins that may be used include, but are not limited to, vaccinia and *E. coli* single strand binding proteins, Herpes simplex virus ICP8 protein, and yeast and human replication Protein A (eg. yRPA and hRPA). A skilled person would be able to readily identify other suitable stimulatory factors that may be usefully combined with a DNA polymerase in the methods of the invention. In one aspect of the invention, the vaccinia single strand binding protein is used to enhance the yield of a DNA cloning method of the invention employing vaccinia DNA polymerase.

The method of the invention may be used to PCR clone any variety or number of target DNA molecules. The only limitation on size is the capacity of the vector molecule to carry the insert in transformation and replication in the host cell. Any vector capable of replicating in a prokaryotic or eukaryotic cell is usable with the present invention, such as plasmids, cosmids, phage, BACs and the like. The choice of vector depends on the functional properties desired, for example, protein expression, and the host cell to be transformed. Preferably, the vector has a known sequence of about 5 to about 100, preferably about 8 to about 50, most preferably about 10 to about 35 nucleotides, on either side of the chosen restriction enzyme site. The DNA molecules that may be incorporated into a recombinant DNA molecule using the method of the invention may be obtained from genomic DNA of prokaryotic or eukaryotic genomes, as well as from various vectors, including plasmids, cosmids, phage, BACs and the like, using restriction enzyme cleavage. Alternatively, the DNA molecules may also be synthesized by automated synthesis and the like. The nucleic acid may also be derived from RNA species, such as mRNA, tRNA and rRNA, from any species and may first be converted to cDNA by reverse transcriptase and the amplified as described in Sambrook et al. (1989).

The linear DNA molecule to be inserted into a linearized vector using the method of the invention need not be obtained through PCR amplification. Such a molecule may also be prepared by linearization of a circular double strand DNA molecule by restriction enzyme digestion, with subsequent attachment of synthetic oligomer linkers onto the ends, or secondary digestion of an already linear DNA molecule with restriction enzymes, followed by addition of adapter/linkers onto the ends, or by annealing of two appropriately designed synthetic single strand DNA oligomers which can be annealed to form an intact duplex DNA molecule, or any other related method. Incubation of a linear DNA molecule, obtained by such a method, with a linearized vector DNA molecule in the presence of a DNA polymerase, having intrinsic exonuclease activity, will provide the desired recombinant DNA molecule. Therefore the present invention also relates to a method of constructing a recombinant DNA molecule comprising:
  providing a linearized vector DNA molecule;
  providing a linear insert DNA molecule having ends that are substantially complementary to the ends of the linearized vector DNA molecule to which they are to be joined; and
  incubating the linearized vector DNA molecule and linear insert DNA molecule in the presence of a DNA polymerase under conditions where the two DNA molecules are joined;
  wherein the DNA polymerase has intrinsic exonuclease activity and joins the DNA molecules.

Transformation of Recombinant DNA Molecules

The reaction mixture obtained from the incubation of DNA polymerase with the linearized vector and the PCR amplified product may be used directly to transform any host cell using standard transformation procedures. Therefore the present invention also provides a method to produce a recombinant DNA product comprising the steps of:
  providing a linearized vector DNA molecule and a template DNA molecule, each having a first and a second end;
  providing a first primer DNA molecule having a 5' end that comprises nucleotide sequences that will incorporate nucleotide sequences that are complementary to the first end of the linearized vector molecule onto the first end of the template DNA molecule and a 3' end that is designed to hybridize to a suitable location on the first end of the template DNA molecule;
  providing a second primer DNA molecule having a 5' end that comprises nucleotide sequences that will incorporate nucleotide sequences that are complementary to the second end of the linearized vector molecule onto the second end of the template DNA molecule and a 3' end that is designed to hybridize to a suitable location on the second end of the template DNA molecule;
  providing the template DNA molecule using the polymerase chain reaction with the first and second primers to provide a PCR amplified product;
  incubating the PCR amplified product with the linearized vector DNA molecule in the presence of a DNA polymerase to generate a recombinant DNA molecule;
  transforming the recombinant DNA molecule into a host cell; and
  isolating the recombinant DNA product;
  wherein the DNA polymerase has intrinsic exonuclease activity and is capable of performing the DNA joining reaction of the invention. A suitable stimulatory factor may optionally be used in the methods of the invention. For example, one may incubate the PCR amplified product with the linearized vector DNA molecule in the presence of a DNA polymerase and a single strand DNA binding protein to generate a recombinant DNA molecule.

Any variety of cell that is transformable may serve as a host cell, such as *E. coli* SURE, JM105, DH5α, HB101, XL1-blue and the like. Other bacterial hosts may include *Bacillus* or *Pseudomonas* species and the like. By way of example, eukaryotic host cells may include *Saccharoniyces* species. One of the advantages of the present invention is that the method is selective for the correct orientation of the insert DNA. Therefore, host cells that have been transformed by a recombinant vector will have the insert DNA in the correct orientation in that vector.

The invention extends to cover the transformation of host cells with reaction products obtained from the cloning of any linear DNA molecule into a linearized vector molecule using the method of the invention. The linear DNA molecule to be cloned may be prepared using PCR as described above or by linearization of a circular dsDNA molecule by restriction enzyme digestion, with subsequent attachment of synthetic oligomer linkers onto the ends, or secondary digestion of an already linear DNA molecule with restriction enzymes, followed by addition of adapter/linkers onto the ends, or by annealing of two appropriately designed synthetic ssDNA oligomers which can be annealed to form an intact duplex DNA molecule, or any other related method.

Kits

The present invention also provides kits suitable for directionally cloning PCR products (or any other linear DNA molecule with appropriate homologous nucleotides on the ends) into a linearized vector. The kit may comprise, in separate containers, an aliquot of a DNA polymerase having intrinsic exonuclease activity that is capable of performing the DNA joining reaction of the invention and an aliquot of reaction buffer. An aliquot refers to an amount of the component sufficient to perform at least one program of cloning. The DNA polymerase may be provided as a solution of known concentration, in a buffer optionally comprising a suitable stabilizer, or may be provided as a predetermined aliquot of a freeze-dried product for dissolution in a suitable buffer. Optionally, the kit may comprise an aliquot of a stimulatory factor such as a single strand DNA binding protein. The kit may also comprise reagents required to perform a positive control reaction. Such reagents may include, in separate containers, an aliquot of linearized vector, an aliquot of insert DNA with first and second ends having appropriate complementary sequences, an aliquot of DNA polymerase having intrinsic exonuclease activity that is capable of performing the DNA joining reaction of the invention, optionally, an aliquot of a stimulatory factor such as a single strand DNA binding protein, and an aliquot of reaction buffer.

The present invention will be further illustrated in the following examples. However, it is to be understood that these examples are for illustrative purposes only, and should not be used to limit the scope of the present invention in any manner.

EXPERIMENTAL EXAMPLES

Materials and Methods

Linear substrates were prepared by restriction enzyme digestion of plasmid pDW101, followed by phenol extraction and ethanol precipitation. pDW101 derives from pBluescript (KS+) (Stratagene) through a spontaneous deletion of nucleotides 618, 619 and 621. In some experiments, the linear substrates were purified by agarose electrophoresis and extracted from the agarose using a Geneclean II kit (New England Biolabs). [$\alpha$-$^{32}$P] dCTP and [$\gamma$-$^{32}$P] dATP were purchased from NEN/Mandel Scientific. End labeled substrates were generated by treatment with shrimp alkaline phosphatase (United States Biochemical, Cleveland), followed by incubation with either T4 polynucleotide kinase and [$\gamma$-$^{32}$P] dATP (3000 Ci/mmol) or Klenow enzyme and [$\alpha$-$^{32}$P] dCTP (3000 Ci/mmol). Unincorporated radionucleotides were removed by G-25 spin columns (Pharmacia) and radioactivity was quantitated by Cherenkov (Schneider, 1971). HindIII-digested lambda phage DNA and HaeIII-digested ΦX174 DNA markers were purchased from New England Biolabs. Luciferase assay kit was purchased from Promega.

Cell and Virus Culture

BSC-40 cells were kindly provided by Dr. E. Niles (SUNY, Buffalo) and grown at 37° C. in DMEM (Gibco BRL) supplemented with 1% nonessential amino acids and 5% fetal calf serum in a 5% $CO_2$ environment. Vaccinia virus (strain WR) was purchased from the ATCC.

Experiment 1

Vaccinia DNA Polymerase Purification

Purification of vaccinia DNA polymerase from vaccinia-infected BSC-40 cells has been described (McDonald and Traktman 1994; Willer, Mann et al. 1999). Briefly, a crude lysate from 60 150-cm² dishes of BSC40 cells co-infected with vTMPOL and VTF7. was subjected to purification through DEAE cellulose, phosphocellulose, ceramic hydroxyapatite and HiTrap heparin columns. Active fractions eluting at each chromatographic step were determined by DNA polymerase assays (Willer, Mann et al. 1999). Protein purity was determined by silver staining of denaturing polyacrylamide gels. Protein concentrations were assayed by using a dye-binding assay (Biorad) and a bovine serum albumin standard.

Experiment 2

Assay for Correct DNA Polymerase Activity

We measure the intrinsic strand joining activity of DNA polymerases, such as those encoded by bacteriophage (e.g. T4, T7), bacteria (e.g. E. coli), fungi (e.g. S. cerevisiae) and viruses (e.g. poxviruses, herpes viruses, adenoviruses, African swine fever virus and other Iridoviruses, and Bacculoviruses). The polymerases are assayed to measure their activity in the DNA joining reaction by incubating a reaction mixture comprising 30 mM Tris-HCl (pH 7.9 ), 5 mM $MgCl_2$, 70 mM NaCl, 1.8 mM dithiothreitol, 88 µg/mL acetylated BSA, 350 ng of each of a first and second linear DNA substrate and the polymerase to be assayed. The first and second linear DNA substrate must have complementary nucleotide sequences on their right and left ends respectively and may be obtained by a variety of methods including chemical synthesis and derivation of nucleic acid fragments from native nucleic acid sequences existing as genes, or parts of genes, in a genome, plasmid, or other vector, such as by restriction endonuclease digest (see, for e.g. preparation of linear substrates described in the Materials and Methods section above). The polymerase has the required activity if the formation of dimers is detected on an agarose gel stained with ethidium bromide. A preferred polymerase will allow the formation of more than about 1% of dimeric products.

Experiment 3

DNA Joining Reactions

Standard DNA joining reactions (20 µL) contained 30 mM Tris-HCl (pH 7.9), 5 mM $MgCl_2$, 70 mM NaCl, 1.8 mM dithiothreitol, 88 µg/mL acetylated BSA, 350 ng of each linear substrate, and varying quantities (usually 0.1 µg) of purified vaccinia DNA polymerase. DNA joining reactions employing single strand binding protein also included 25 µg/mL of recombinant vaccinia single strand binding protein (thought to be the IL3 gene product, Tseng et al. 1999) in the reaction mix. Reactions were incubated at 37° C. for 20 min, deproteinized and the reaction products were separated through a 0.8% agarose gel as described previously (Zhang and Evans, 1993). Ethidium- stained gels were photographed under UV illumination using Polaroid 665 film. DNA quantitation was determined by desitometry.

Joining of Two Linear Substrates:

To show that vaccinia DNA polymerase can catalyze strand joining reactions, two linear duplex substrates, sharing a small amount of overlapping sequence homology at the ends of the molecules, were prepared. This was accomplished by cutting pDW101 (SEQ. ID. NO. 1) with EcoRI (SEQ. ID. NO. 2) and XhoI (SEQ. ID. NO. b 3) (FIG. 1A), leaving 33 bp of properly oriented sequences. DNA polymerase was then incubated with these DNAs and assayed for concatemer-forming activity using gel electrophoresis. It observed that the polymerase converted 45% of the input DNA into dimeric products over a 10 min period, with a concomitant loss of monomeric molecules (FIG. 1B). The yield of dimer declined slightly thereafter, stabilizing with about 35% of the molecules converted to product. The reaction yield was also dependent upon protein concentration (FIG. 1C).

Figure 5:
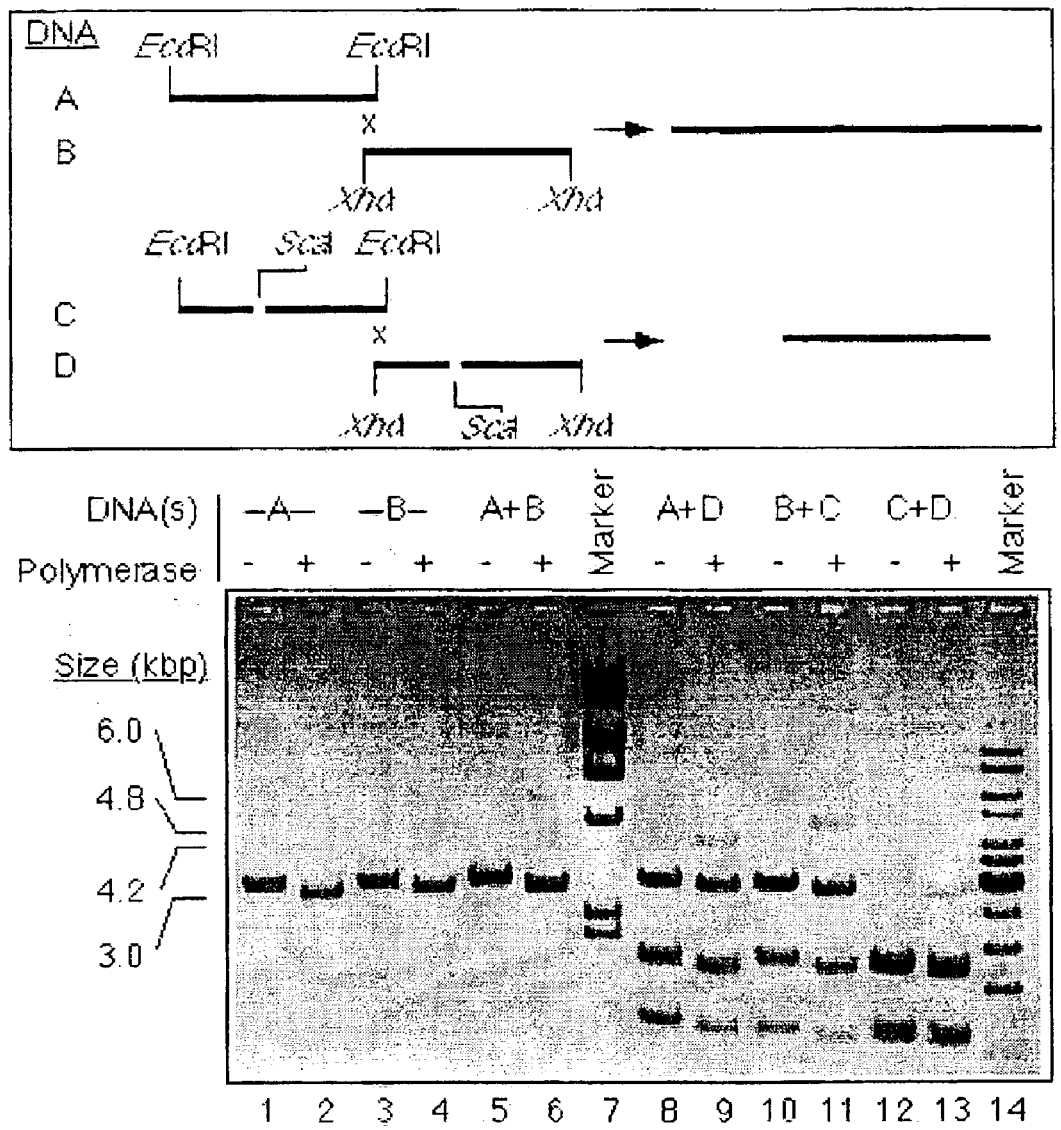
FIG. 5 shows a schematic representation and the experimental results for assays investigating the effect of overlapping and non-overlapping end homology in the DNA joining method of the invention.

Duplex Annealing Selectively Pairs Homologous Ends:

This pairing reaction required two different DNA substrates sharing some small amount of overlapping end homology. Controls showed that the reaction cannot produce joint molecules when the only available substrates were a pool of identical duplexes (FIG. 5, lanes 1-6). To determine which ends of the two substrates were being joined, EcoRI and XhoI cut molecules were further digested with Sca, producing DNA fragments that can be differentiated by size (FIG. 5, inset). Vaccinia DNA polymerase selectively joined the two molecules sharing a segment of DNA bounded by the XhoI and EcoRI sites, as judged by the appearance of recombinants 4.2, 4.8, and 3.0 kbp in length (FIG. 5, lanes 9, 11, and 13, respectively). Such product sizes are consistent with these molecules being composed of the 3.0+1.2, 3.0+1.8, and 1.2+1.8 kbp DNA fragments encoding the XhoI-EcoRI interval.

The restriction enzymes used to prepare the interacting ends shown in FIGS. 1 and 5 leave 5'-overhanging ends with 4 nt overhangs. To test whether ends also affected reaction efficiency, various substrates were prepared by cutting pDW101 with different restriction enzymes. All possible combinations of molecules bearing 5'-overhanging, blunt, or 5'-recessed ends were then tested to see whether they were still substrates. It was found that vaccinia polymerase has no end preference. There was also no obvious correlation between the yield of duplex product and the length of sequence overlap, when the length of shared end homology ranged from 18 to 84 bp.

Figure 6:
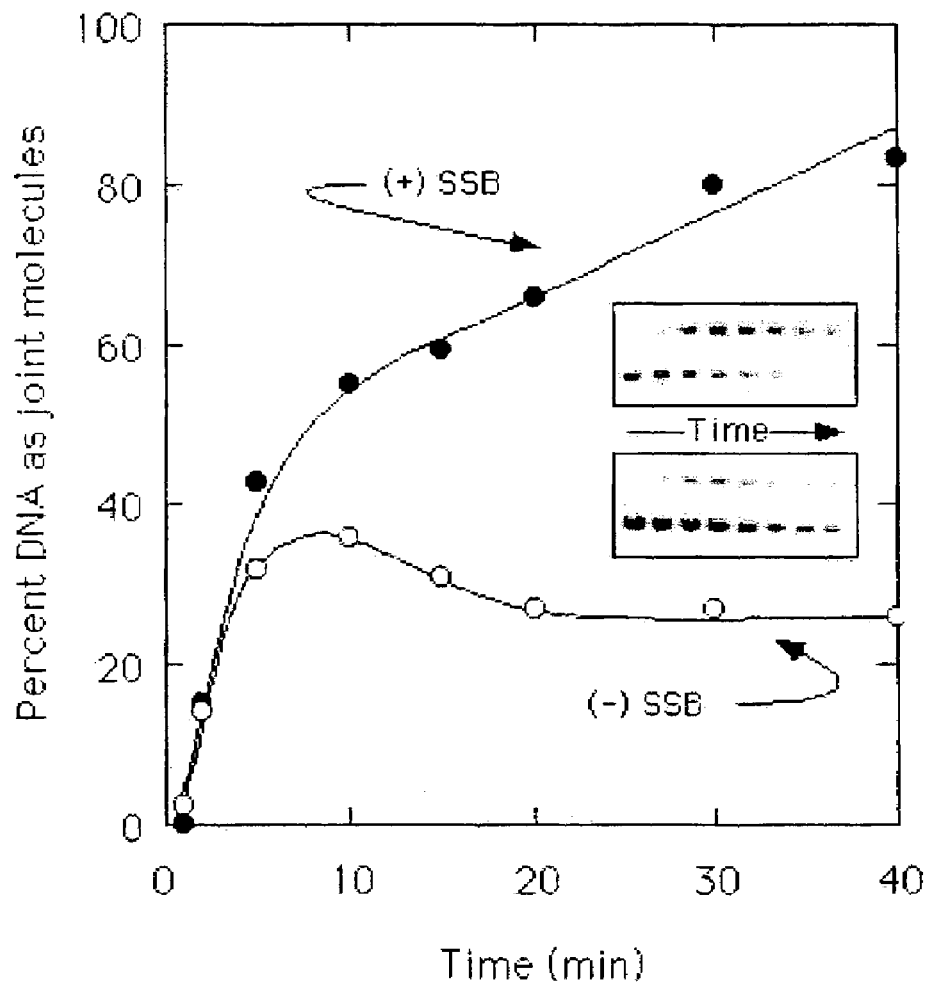
FIG. 6 is a graph and experimental results (inset) showing the effect of vaccinia single strand binding protein on joint molecule formation using the method of the invention.

Other Reactions:

The effect of adding $MgCl_2$, spermidine, or vaccinia virus single strand binging protein (SSB) on the reaction efficiency was examined using KpnI- and NotI-cut substrates sharing 84 bp of overlapping homology. Magnesium had a reaction optimum of ~10 mM. However, 20 mM $MgCl_2$ inhibited the reaction, as did spermidine concentrations exceeding 1 mM. The effects of adding recombinant vaccinia SSB (Tseng et al. 1999) were investigated,. The principle replicative high-affinity single-strand DNA binding protein (SSB) is thought to be the I3L gene product (Rochester and Traktman, 1998; Tseng et al. 1999). Vaccinia SSB enhanced the yield of joint molecules 2-3-fold when added at concentrations between 25 and 100 μg/mL (FIG. 6). The net result was that over 80% of the substrate DNAs could be converted to dimers under these optimized reaction conditions.

Figure 7:
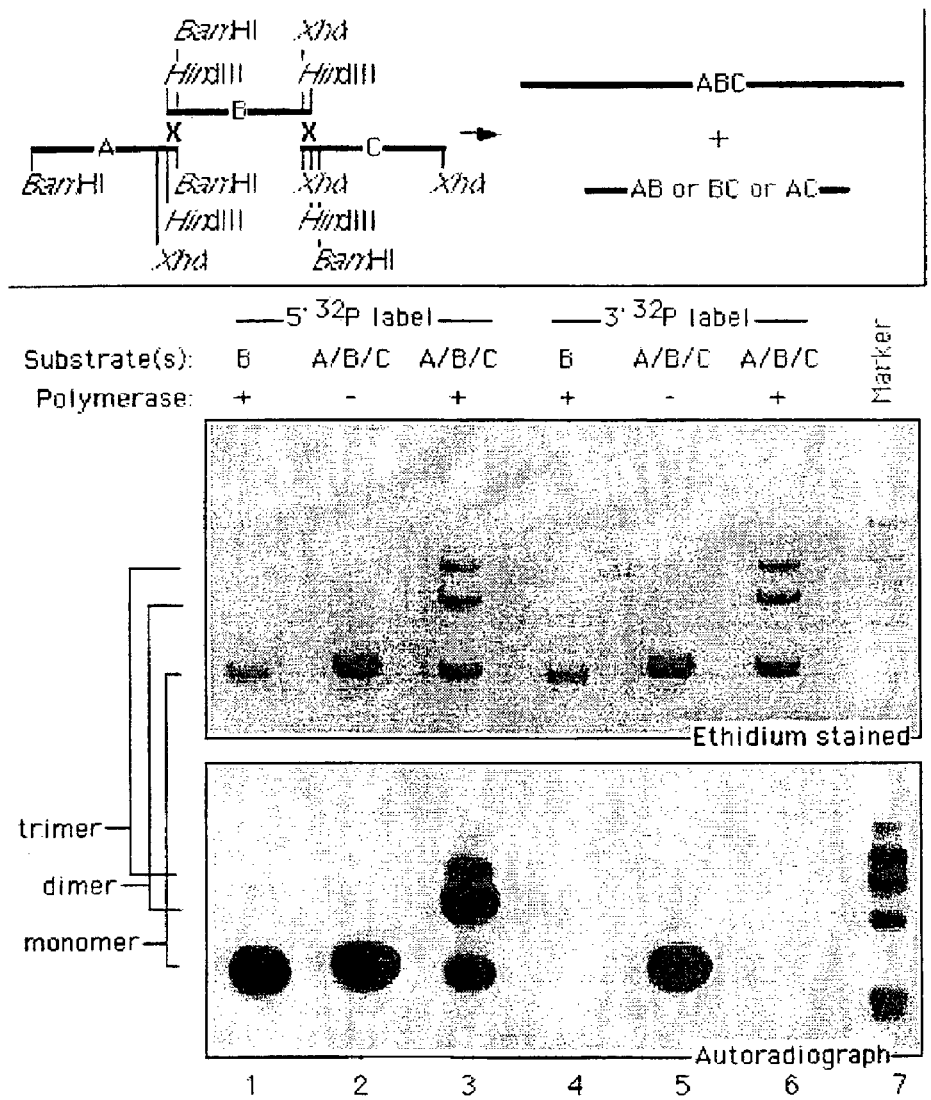
FIG. 7 provides a schematic representation and experimental results depicting the joining of three linear DNA substrates and the fate of 5'- and 3'-end labels during the joining of three linear DNA molecules using the method of the invention.

Joining of Multiple Substrates:

The DNA-joining reaction can also recombine multiple substrates into higher-order concatemers and this can be exploited to provide further insights into the reaction mechanism. The plasmid pDW101 was cut with restriction enzymes so that the "middle" substrate (FIG. 7, molecule "B") shared sequences in common with either end of two additional molecules ("A" and "C"). Alone, the middle duplex was not a substrate for the polymerase catalyzed reaction (FIG. 7, lanes 1 and 4). However, when the three substrates were incubated together with vaccinia polymerase in standard assays, they were rapidly converted into a mixture of dimers and trimers (FIG. 7, lanes 3 and 6). A small amount of the DNA (~2%) was also converted into higher-order multimers whose structure is uncertain.

For the middle molecule to have been incorporated into a linear trimer, both ends of the molecule must have been subjected to enzymatic processing. To study any modifications which might have been introduced into the ends of these molecules, the HindIII-restricted (SEQ. ID. NO. b 4) substrate was labeled and monitored the $^{32}P$-label using autoradiography. The $^{32}P$-labels were incorporated into the middle substrates using T4 polynucleotide kinase or Klenow polymerase, to see whether 3' or 5' end-labels suffered different fates. After electrophoresis and ethidium staining, the gel was fixed and autoradiographed to locate the label. It was clear, from inspection of the ethidium-stained gel, that duplex "B" was efficiently incorporated into concatemers regardless of whether it had been labeled on the 3' or on the 5' end (FIG. 7, lanes 3 and 6). However, whereas most of the 5' label was incorporated into trimeric concatemers (FIG. 7, lane 3), none of the 3'-end label was retained in these molecules (FIG. 7, lane 6) or in the unreacted polymerase-treated substrate (FIG. 7, lane 4). These data, plus the $MgCl_2$ effect, suggests that the vaccinia polymerase 3'-5' exonuclease plays a key role in joint molecule production in vitro. Although it is the 3'-5' exonuclease activity of vaccinia DNA polymerase that plays a pivotal roll in the DNA joining reactions described herein, the reaction could work equally as well with DNA polymerases having 5'-3' exonuclease activity.

If this reaction is dependent upon the activity of the 3'-5' exonuclease of vaccinia DNA polymerase, one would predict that dNTPs should inhibit end-joining by inhibiting the nuclease. Experiments confirmed this prediction. Adding 1 μM (total) of all four dNTPs reduced the yield about 50%, while little if any joint molecules were formed in reactions containing >5 μM dNTPs. Dideoxyribonucleotides were also inhibitory, but only at much higher concentrations (>50 μM).

Example 4

PCR Step

A ~800 bp region from a BamHI clone-derived from Shope Fibroma Virus (Wills, Delange et al. 1983; Delange, Macaulay et al 1984) chosen at random was amplified using the PCR primers shown below. Capital letters represent the sequence complementary to the vector (pDW101) and small letters represent the sequence complementary to viral DNA sequence. PCR primers were designed to include complementary sequences from the vector adjacent to the recognition site for the restriction enzyme NotI.

```
Primer #1:  5' TTCTAGAGCGGCCagaaacaggcatcttacgcgtg 3' (SEQ.ID.NO.5)

Primer #2:  5' TCCACCGCGGTGGCGGCCacggaaacgccttggt 3' (SEQ.ID.NO.6)
```

Example 5

Vector Preparation

The vector pDW101 was digested with NotI as depicted below:

(SEQ.ID.NO.7)

Example 6

Generation of Recombinant Molecules

Figure 8:
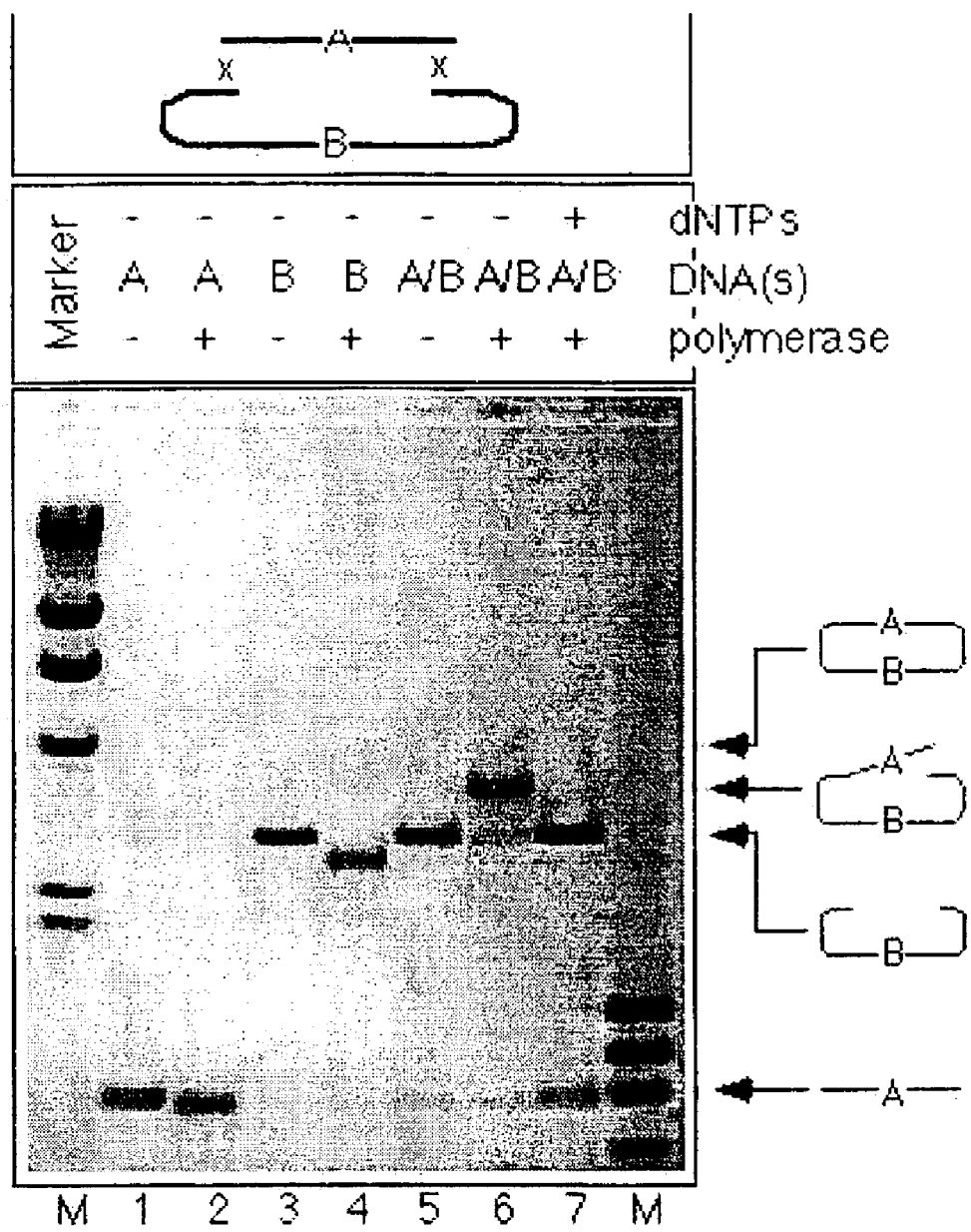
FIG. 8 provides schematic and experimental results for the cloning of PCR-amplified DNA using the method of the invention.

Both the PCR amplified fragment (320 ng) and the linearized vector (600 ng) were incubated together in the presence of purified vaccinia DNA polymerase (150 ng) for 20 minutes as per the annealing assay described in the Materials and Methods. Reaction products were visualized by agarose electrophoresis (FIG. 8). Agarose gels showed that the majority of molecules formed under these conditions were the linear-dimers seen previously (FIG. 8, lane 5). However, because both ends of the PCR-amplified insert shared homology with the vector, a small portion of the reaction products were expected to, and did, migrate at positions characteristic of nicked-circular and higher concatemer forms (FIG. 8, lane 6). None of these reactions occurred in the presence of 5 μM dNTP (FIG. 8, lane 7).

Example 7

Transformation of Competent Cells

An aliquot (1-2 μL) of the reaction mixture from Example 6 was used to transform three different strains of E. coli (SURE, JM105 and DH5α) using standard procedures (SURE and DH5α, by electroporation and JM105, by heat shock). Appropriate dilutions were plated on LB+T plates containing 100 μg/mL ampicillan, 40 μg/mL X-gal (5-bromo-4-chloro-3-indolyl-β-D-galactoside), 0.5 mM IPTG (isopropylthio-β-galactoside) and 50 μg/mL thymine and incubated overnight at 37° C. DNA was isolated from transformed colonies and sequenced as described previously (Willer, McFadden and Evans, 1999

Table 1 shows data acquired using multiply-recombination deficient SURE cells, although all three strains gave similar results ($0.5-2\times10^5$ transformants per μg). White (W) colonies indicate transformation with potentially the correct construct. Blue (B) colonies indicate transformation with the vector substrate alone. It was clear that the yield of stable transformants was greatly dependent upon adding vaccinia DNA polymerase to the reaction mix. Recombinant (white) colonies were the most abundant product (83% of transformants in this particular experiment) even though the NotI-cut vector was not dephosphorylated. Thirteen putative recombinant plasmids were purified and it was observed that all 13 of the plasmids recovered from SURE cells were monomers incorporating a single DNA insert. DNA sequencing showed that all 13 molecules also encoded the insert in the correct orientation and at the expected position. There were 3 base substitutions located within one of the primer-binding sites and 2 other mutations within Taq polymerase-amplified DNA. The fusion points were those expected to be formed through annealing of homologous ends. It was concluded that the concatemers assembled by vaccinia virus polymerase can be processed into stable recombinants with a fidelity comparable to traditional cloning methods.

TABLE 1

Transformation of E. coli with recombinant joint molecules.

| Reaction | Number of colonies White | Number of colonies Blue | Percent white | Transformants per μg ($\times10^{-5}$) |
|---|---|---|---|---|
| PCR-amplified insert | | | | |
| (−) polymerase | 2 | 0 | 100 | N/A |
| (+) polymerase | 1 | 0 | 100 | N/A |
| NotI restricted vector | | | | |
| (−) polymerase | 8 | 1,190 | 0.7 | 4.0 |
| (+) polymerase | 0 | 27 | 0.0 | 0.4 |
| PCR-amplified insert plus NotI restricted vector | | | | |
| (−) polymerase | 12 | 1,030 | 1.2 | 2.3 |
| (+) polymerase | 1,020 | 210 | 83 | 2.7 |
| (+) polymerase, (+) dNTP | 7 | 220 | 3.1 | 0.5 |

Joint molecules were prepared in reactions containing the indicated reaction components. E. coli SURE cells were electroporated with 1 μL of reaction products. The cells (100 μL or its equivalent) were plated and colonies were counted next day. Cell competency was estimated as $6 \times 10^{10}$ transformants per μg using unrestricted pDW101.

Example 8

The Minimal Sequence Overlap

Figure 9:
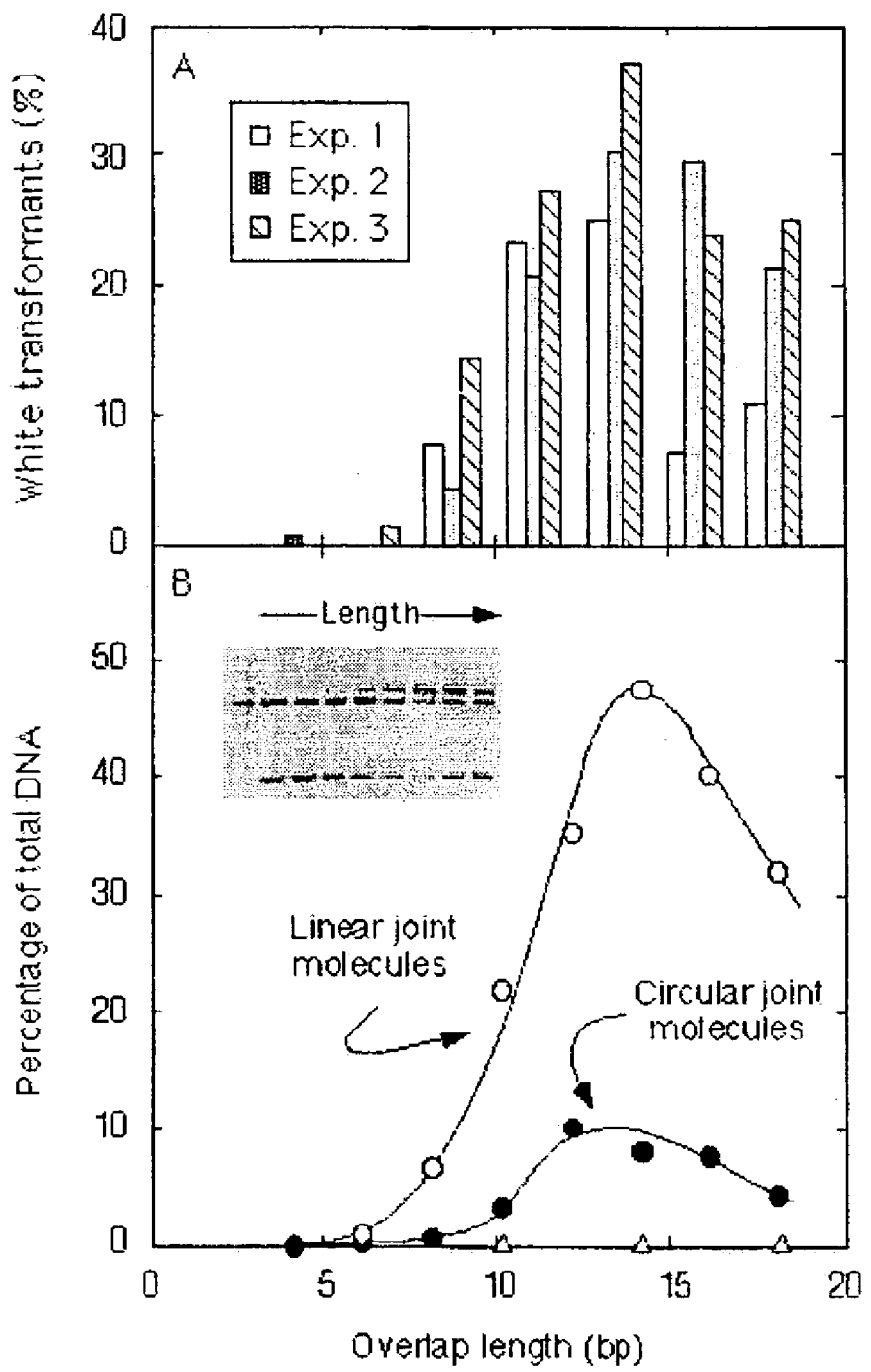
FIG. 9 shows a graphical representation of the effect of homology length on joint molecule formation in the method of the invention.

To determine the minimal amount of homology required for production of joint molecules, seven additional primer pairs were synthesized and then the set of eight oligonucleotide pairs were used to again PCR amplify a ~800 bp fragment of SFV DNA. These 14 new PCR primers were similar in structure to the primers described above, except that the amount of sequence homologous to nucleotides flanking the NotI site in a NotI-cut vector now ranged from 4 to 18 bp. These substrates were incubated with vector DNA in optimized assays containing both vaccinia DNA polymerase and gpI3L (which increased the ability to detect otherwise faint circular reaction products) and the yield of both linear and circular joint molecules were quantitated using densitometry. These and other experiments showed that as little as 10 bp of sequence homology between substrates still permitted strand joining by vaccinia polymerase, with a reaction optimum of about 14 bp (FIG. 9, panel B). These reaction products were also used to transform SURE cells, in triplicate, as there was some variation in the absolute efficiency of white transformant production from experiment to experiment. In all of the experiments, the percentage of white (recombinant) bacterial transformants closely paralleled the yield of joint molecules as detected by gel electrophoresis (FIG. 9A).

Example 9

Cloning a Recombinant Plasmid DNA with Vaccinia Virus DNA Polymerase

Figure 10:
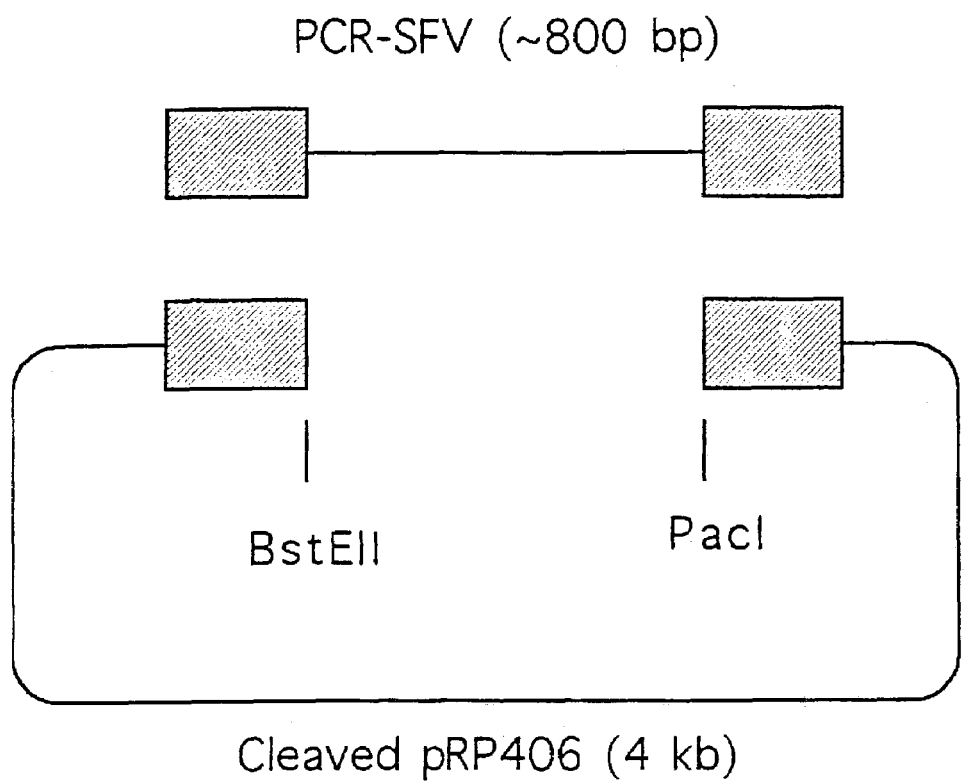
FIG. 10 provides a map of DNA to be recombined to clone a recombinant DNA pRP406-SFV using the method of the invention.

The method of the invention was successfully utilized to clone a recombinant DNA pRP406-SFV (FIG. 10, 11).

The cloning method of the present invention was compared with a traditional cloning method. Overall, the method of the present invention was simpler and quicker (Table 2).

Vector: pRP406 (SEQ. ID. NO. 8) was cut with PacI and BstEII and the larger fragment was purified to eliminate the smaller, intervening fragment.

Insert: PCR-SFV(~800 bp, SEQ. ID. NO. 9),the polymerase chain reaction was used to amplify a fragment of Shope fibroma virus DNA. PCR primers added 16 bp sequences at the ends of the DNA that were homologous to sequences located at the ends of the cut vector (FIG. 10). Primers used when recombining DNA with pRP406 are shown in SEQ. ID. NOs. 10 and 11.

TABLE 2

Comparison of Cloning Strategies

|  | Joining by v DNA pol | Traditional method with ligase |
|---|---|---|
| PCR-amplified insert | With >12 nt homology with linear vector at both ends 300 ng, 600 fmol | Cleaved with BstEII and Pac I to generate the sticky ends 150 ng, 300 fmol |
| Linear vector | 250 ng, 100 fmol | 100 ng, 40 fmol |
| Reaction condition | v pol 100 ng, v SSB 500 ng in 20 ul 37° C. 10 min | T4 DNA ligase 5 U in 10 ul 20° C. 2 hr |
| Transformation | 1 of 20$^{th}$ of reaction solution into *E. coli* SURE | 1 of 10$^{th}$ of reaction solution into *E. coli* SURE |
| Recombinant frequency | 4.8 × 10$^4$/ug vector | 9.2 × 10$^4$/ug vector |

While the present application has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

Full Citations for References Referred to in the Specification

Ailenberg, M. and M. Silverman (1996). "Description of a one step staggered reannealing method for directional cloning of PCR-generated DNA using sticky-end ligation without employing restriction enzymes." *Biochem Mol Biol Int* 39(4): 771-9.

Aguado, B. Selmes, I. P. and Smith, G. L. (1992). Nucleotide sequence of 21.8 kbp of variola major virus strain Harvey and comparison with vaccinia virus. *J Gen Virol* 73, 2887-902.

Aslanidis, C. and P. J. de Jong (1990). "Ligation-independent cloning of PCR products (LIC-PCR)." *Nucleic Acids Res* 18(20): 6069-74.

Ball, L. A. (1987). High-frequency homologous recombination in vaccinia virus DNA. *J Virol* 61, 1788-95.

Bubeck, P., M. Winkler, et al. (1993). "Rapid cloning by homologous recombination in vivo." *Nucleic Acids Res* 21(15): 3601-2.

Cha, J., W. Bishai, et al. (1993). "New vectors for direct cloning of PCR products [published erratum appears in Gene 1994 Apr 8;141(1):149]." *Gene* 136(1-2): 369-70.

Challberg, M. D. and Englund, P. T. (1979). Purification and properties of the deoxyribonucleic acid polymerase induced by vaccinia virus. *J Biol Chem* 254, 7812-9.

Clark, J. M. (1988). "Novel non-templated nucleotide addition reactions catalyzed by procaryotic and eucaryotic DNA polymerases." *Nucleic Acids Res* 16(20): 9677-86.

Colinas, R., J. Condit, R. C., and Paoletti, E. (1990). Extrachromosomal recombination in vaccinia-infected cells requires a functional DNA polymerase participating at a level other than DNA replication. *Virus Res* 18, 49-70.

Costa, G. L. and M. P. Weiner (1994). "Polishing with T4 or Pfu polymerase increases the efficiency of cloning of PCR fragments." *Nucleic Acids Res* 22(12): 2423.

Du, S., and Traktman, P. (1996). Vaccinia virus DNA replication: two hundred base pairs of telomeric sequence confer optimal replication efficiency on minichromosome templates. *Proc Natl Acad Sci USA* 93, 9693-8.

DeLange, A. M. (1989). Identification of temperature-sensitive mutants of vaccinia virus that are defective in conversion of concatemeric replicative intermediates to the mature linear DNA genome. *J Virol* 63, 2437-44.

DeLange, A. M., and McFadden, G. (1986). Sequence-nonspecific replication of transfected plasmid DNA in poxvirus-infected cells. *Proc Natl Acad Sci U S A* 83, 614-8.

Delange, A. M., C. Macaulay, et al. (1984). "Tumorigenic poxviruses: construction of the composite map of the Shope fibroma virus genome." *J. Virol* 50(2):408-416.

Duncan, B. K. and J. A. Chambers (1984). "The cloning and overproduction of *Escherichia coli* uracil-DNA glycosylase." *Gene* 28(2): 211-9.

Evans, D. H., Stuart, D., and McFadden, G. (1988). High levels of genetic recombination among cotransfected plasmid DNAs in poxvirus-infected mammalian cells. *J Virol* 62, 367-75.

Fisher, C. Parks, R. J., Lauzon, M. L., and Evans, D. H. (1991). Heteroduplex DNA formation is associated with replication and recombination in poxvirus-infected cells. *Genetics* 129, 7-18.

Gal, J., R. Schnell, et al. (1999). "Directional cloning of native PCR products with preformed sticky ends (autosticky PCR)." *Mol Gen Genet* 260(6): 569-73.

Garces, C. and J. Laborda (1995). "Single-step, ligase-free cloning of polymerase chain reaction products into any restriction site of any DNA plasmid." *Anal Biochem* 230 (1): 178-80.

Guthrie, C. and Fink, G. (1991). Methods in Enzymology. 194.

Hanahan, D. (1985). In: DNA Cloning, Vol I. Glover, D. M. (ed.), IRL Press, Oxford.

Haun, R. S., I. M. Serventi, et al. (1992). "Rapid, reliable ligation-independent cloning of PCR products using modified plasmid vectors." *Biotechniques* 13(4): 515-8.

Hendricks, S. P., and Mathews, C. K. (1998). Allosteric regulation of vaccinia virus ribonucleotide reductase, analyzed by simultaneous monitoring of its four activities. *J Biol Chem* 273, 29512-8.

Hengen, P. N. (1995). "Methods and reagents. Cloning PCR products using T-vectors." *Trends Biochem Sci* 20(2): 85-6.

Howell, M. L., Roseman, N. A., Slabaugh, M. B., and Mathews, C. K. (1993). Vaccinia virus ribonucleotide reductase. Correlation between deoxyribonucleotide supply and demand. *J Biol Chem* 268, 7155-62.

Hsiao, K. (1993). "Exonuclease III induced ligase-free directional subcloning of PCR products." *Nucleic Acids Res* 21(23): 5528-9.

Ichihara, Y. and Y. Kurosawa (1993). "Construction of new T vectors for direct cloning of PCR products." *Gene* 130(1): 153-4.

Johnson, G. P., Goebel, S. J. and Paoletti, E. (1993). An update on the vaccinia virus genome. *Virology* 196, 381-401.

Kaluz, S. and A. P. Flint (1994). "Ligation-independent cloning of PCR products with primers containing nonbase residues." *Nucleic Acids Res* 22(22): 4845.

Kaluz, S., K. Kolble, et al. (1992). "Directional cloning of PCR products using exonuclease III." *Nucleic Acids Res* 20(16): 4369-70.

Karakousis, G., Ye, N., Li, Z., Chiu, S. K., Reddy, G., and Radding, C. M. (1998). The beta protein of phage lambda binds preferentially to an intermediate in DNA renaturation. *J Mol Biol* 276, 721-31.

Kaufman, D. L. and G. A. Evans (1990). "Restriction endonuclease cleavage at the termini of PCR products [published erratum appears in Biotechniques 1990 Dec;9(6): 720]." *Biotechniques* 9(3): 304, 306.

Kovalic, D., J. H. Kwak, et al. (1991). "General method for direct cloning of DNA fragments generated by the polymerase chain reaction." *Nucleic Acids Res* 19(16): 4560.

Kuijper, J., L. K. M. Wiren. et al. (1992). "Functional cloning vectors for use in directional cDNA cloning using cohesive ends produced with T4 DNA polymerase." *Gene* -112(2): 147-55.

Li, Z., Karakousis, G., Chiu, S. K., Reddy, G., and Radding, C. M. (1998). The beta protein of phage lambda promotes strand exchange. *J Mol Biol* 276, 733-44.

Liu, Z. (1996). "Hetero-stagger cloning: efficient and rapid cloning of PCR products." *Nucleic Acids Res* 24(12): 2458-9.

Liu, Z. G. and L. M. Schwartz (1992). "An efficient method for blunt-end ligation of PCR products." *Biotechniques* 12(1): 28, 30.

Longo, M. C., M. S. Berninger, et al. (1990). "Use of uracil DNA glycosylase to control carry-over contamination in polymerase chain reactions." *Gene* 93(1): 125-8.

McDonald, W. F. and Traktman, P. (1994). "Analysis of the complete genome of smallpox variola major virus strain Bangladesh-1975." *Virology* 201(2): 215-240.

McFadden, G., and Dales, S. (1979). Biogenesis of poxviruses: mirror-image deletions in vaccinia virus DNA. *Cell* 18, 101-8.

McDonald, W. F., and Traktman, P. (1994). Overexpression and purification of the vaccinia virus DNA polymerase. *Protein Expr Purif* 5, 409-21.

Mead, D. A., N. K. Pey, et al. (1991). "A universal method for the direct cloning of PCR amplified nucleic acid." *Biotechnology* (N Y) 9(7): 657-63.

Merchlinsky, M. (1989). Intramolecular homologous recombination in cells infected with temperature-sensitive mutants of vaccinia virus. *J Virol* 63, 2030-5.

Moss, B. (1996). Poxviridae: The viruses and their replication. 3rd. ed. In "Fundamental Virology" (B. N. Fields, Knipe, D. M. Howley. P. M. Ed.), pp. 1163-1197. Raven, Philadelphia.

Mole, S. E., R. D. Iggo, et al. (1989). "Using the polymerase chain reaction to modify expression plasmids for epitope mapping." *Nucleic Acids Res* 17(8): 3319.

Moyer, R. W., and Graves, R. L. (1981). The mechanism of cytoplasmic orthopoxvirus DNA replication. *Cell* 27, 391-401.

Mullis, K. B. and F. A. Faloona (1987). "Specific synthesis of DNA in vitro via a polymerase-catalyzed chain reaction." *Methods Enzymol* 155: 335-50.

Oliner, J. D., K. W. Kinzler, et al. (1993). "In vivo cloning of PCR products in *E. coli.*" *Nucleic Acids Res* 21(22): 5192-7.

Paques, F., and Haber, J. E. (1999). Multiple pathways of recombination induced by double-strand breaks in *Saccharomyces cerevisiae*. *Microbiol Mol Biol Rev* 63, 349-404.

Parks, R. J., and Evans, D. H. (1991). Effect of marker distance and orientation on recombinant formation in poxvirus-infected cells. *J Virol* 65, 1263-72.

Pickup, D. J., Bastia, D., Stone, H. O., and Joklik, W. K. (1982). Sequence of terminal regions of cowpox virus DNA: arrangement of repeated and unique sequence elements. *Proc Natl Acad Sci USA* 79 7112-6.

Rashtchian, A., G. W. Buchman, et al. (1992). "Uracil DNA glycosylase-mediated cloning of polymerase chain reaction- amplified DNA: application to genomic and cDNA cloning." *Anal Biochem* 206(1): 91-7.

Rochester, S. C., and Traktman, P. (1998). Characterization of the single-stranded DNA binding protein encoded by the vaccinia virus 13 gene. *J Virol* 72, 2917-26.

Rosemond-Hornbeak, H., and Moss, B. (1974). Single-stranded deoxyribonucleic acid-specific nuclease from vaccinia virus. Endonucleolytic and exonucleolytic activities. *J Biol Chem* 249, 3292-6.

Saiki. R. K., D. H. Gelfand, et al. (1988). "Primer-directed enzymatic amplification of DNA with a thermostable DNA polymerase." *Science* 239(4839): 487-91.

Sambrook et al. (1989). "Molecular cloning: A laboratory manual." Cold Spring Harbour, N.Y.

Scharer, E. and R. Iggo (1992). "Mammalian p53 can function as a transcription factor in yeast." *Nucleic Acids Res* 20(7): 1539-45.

Scharf, S. J. (1990). In Innis, M. A., Gelfand, D. H., Sninsky, J. J., and White, T. J. (Eds.) , PCR Protocols. Academic Press, New York, pp. 84-91.

Schneider, P. B. (1971). "Determination of specific activity of 32P-labeled compounds using Cernkov counting." *J Nucl Med* 12(1): 14-16.

Shchelkunov, S. N., and Totmenin, A. V. (1995). Two types of deletions in orthopoxvirus genomes. *Virus Genes* 9, 231-45.

Shuldiner, A. R., K. Tanner, et al. (1991). "Ligase-free subcloning: a versatile method to subclone polymerase chain reaction (PCR) products in a single day." *Anal Biochem* 194(1): 9-15.

Shuman, S. (1991). "Site-specific DNA cleavage by vaccinia virus DNA topoisomerase I. Role of nucleotide sequence and DNA secondary structure." *J Biol Chem* 266(3): 1796-803.

Shuman, S. (1992). "DNA strand transfer reactions catalyzed by vaccinia topoisomerase I." *J Biol Chem* 267(12): 8620-7.

Shuman, S. (1992). "Two classes of DNA end-joining reactions catalyzed by vaccinia topoisomerase I." *J Biol Chem* 267(24): 16755-8.

Shuman, S. (1994). "Novel approach to molecular cloning and polynucleotide synthesis using vaccinia DNA topoisomerase." *J Biol Chem* 269(51): 32678-84.

Shuman, S. and J. Prescott (1990). "Specific DNA cleavage and binding by vaccinia virus DNA topoisomerase I." *J Biol Chem* 265(29): 17826-36.

Stahl, M. M., Thomason, L., Poteete, A. R., Tarkowski, T., Kuzminov, A., and Stahl, F. W. (1997). Annealing vs. invasion in phase lambda recombination. *Genetics* 147, 961-77.

Stivers, J. T., S. Shuman, et al. (1994). "Vaccinia DNA topoisomerase I: single-turnover and steady-state kinetic analysis of the DNA strand cleavage and ligation reactions." *Biochemistry* 33(1): 327-39.

Temesgen, B. and K. Eschrich (1996). "Simplified method for ligase-free cloning of PCR products." Biotechniques 21(5): 828, 830, 832.

Traktman, P. (1990). The enzymology of poxvirus DNA replication. *Curr Top Microbiol Immunol* 163, 93-123.

Tseng, M., Palaniyar, N., Zhang, W., and Evans, D. H. (1999). DNA binding, aggregation, and annealing properties of the vaccinia virus I3L gene product. *J Biol Chem* 274, 21637-44.

Varshney, U. and J. H. van de Sande (1991). "Specificities and kinetics of uracil excision from uracil-containing DNA oligomers by *Escherichia coli* uracil DNA glycosylase." *Biochemistry* 30(16): 4055-61.

Weiner, M. P. (1993). "Directional cloning of blunt-ended PCR products." *Biotechniques* 15(3): 502-5.

Willer, D. O., Mann, M. J. et al. (1999). "Vaccinia virus DNA polymerase promotes DNA pairing and strand transfer reactions." *Virology* 257(2):511-523.

Willer, D. O., McFadden, G., and Evans, D. H. (1999). The complete genome sequence of shope (rabbit) fibroma virus. *Virology* 264, 319-43.

Wills, A., Delange, A. M. et al. (1983). "Physical characterization and molecular cloning of the Shope fibroma virus DNA genome." *Virology* 130(2):403-414.

Zhang, W. and Evans, D. H. (1993). "DNA strand exchange catalyzed by proteins from vaccinia virus-infected cells." *J. Virol* 67(1):204-212.

Zhou, M. and Z. Hatahet (1995). "An improved ligase-free method for directional subcloning of PCR amplified DNA." *Nucleic Acids Res* 23(6): 1089-90.

Detailed Legends for Figures

FIG. 1. DNA annealing catalyzed by vaccinia DNA polymerase. pDW101 was cut with EcoRI or XhoI to produce 2.6 kbp molecules sharing 33 bp of overlapping sequence homology (Panel A.). Annealing reactions (20 µL) were then prepared containing 0.35 µg of each DNA substrate plus 0.1 µg of vaccinia virus polymerase. After incubation for the indicated times, the reaction products were fractionated using agarose gel electrophoresis and visualized by ethidium bromide staining (Panel B). Alternatively, reactions were prepared containing 0.35 µg of each DNA substrate plus the indicated quantities of DNA polymerase and incubated for 20 min at 37° (Panel C.). A 6 kbp reaction product is formed in Panels B and C.

FIG. 2. Trimer formation. Panel A shows a schematic of the reaction. Note that joining three linear molecules is essentially the same reaction needed to join an insert DNA to the two flanking arms of a vector molecule. Panel B shows the reaction products analyzed on an ethidium-stained agarose gel. No joint molecules are formed when only one of the three substrates are provided to the polymerase. This shows that the reaction requires correct complementary sequences at the ends of the reacting molecules.

FIG. 3. Combinatorial fusion of DNA cassettes. In this simple scheme three different pools of DNA duplexes are prepared. Within a pool of molecules, the central portion of each molecule varies in sequence while the ends are identical. For example, A1-A5 all have the same ~20 base sequence at the right end but the middle portions of these molecules vary in sequence. The left ends of molecules in the "B" pool are compatible with the right ends of molecules in the "A" pool. Similarity, the left ends of molecules in the "C" pool are compatible with the right ends of molecules in the "B" pool. Reaction with vaccinia polymerase will create trimers composed of one each of molecules selected from the "A", "B", and "C" pools. The resulting pool of trimers should express a random assortment of "A", "B", and "C" variants.

FIG. 4. Proposed cloning method. The PCR primers encode 10-20 additional nucleotides complementary to sequences flanking the vector insertion site.

FIG. 5. Substrate requirements. Reactions were prepared containing the indicated substrate DNAs plus or minus vaccinia DNA polymerase (0. µg) in 20 µL. The polymerase will not promote joint molecule formation unless two substrates are provided which share some overlapping end homology (lanes 1-6). When the DNA fragments can be differentiated by size, the reaction products comprise DNAs encoding the XhoI-EcoRI overlap region (lanes 8-13).

FIG. 6. Effect of vaccinia SSB (gpI3L) on joint molecule formation. Standard reactions (20 µL) contained 0.1 µg of vaccinia virus DNA polymerase (E) or 0.1 µg of polymerase plus 0.5 µg of vaccinia SSB (●). The reactions were incubated for the indicated time, stopped, and the yield of joint molecules determined by gel electrophoresis (inset) and densitometry. Vaccinia SSB increased the extent of the reaction and stabilized the products.

FIG. 7. Trimer formation catalyzed by vaccinia virus DNA polymerase. Three substrates were prepared as indicated in the upper panel and the middle substrate ("B") labeled using polynucleotide kinase or Klenow polymerase. Reactions were prepared as indicated incubated at 37° C. for 20 min, and then fractionated using agarose gel electrophoresis. The reaction products were first visualized with ethidium bromide, and then by autoradiography. No joint molecules were formed in reactions containing polymerase plus only a single DNA substrate (lanes 1 and 4). Only a 5' label survived incubation with the polymerase and was incorporated into dimer and trimer molecules (lane 3).

FIG. 8. Cloning of PCR-amplified DNA using vaccinia virus DNA polymerase. An ~800 bp PCR-amplified DNA fragment ("A") was incubated with or without NotI-linearized pDW101 ("B") and vaccinia virus DNA polymerase, as indicated. The reaction products were separated by electrophoresis and visualized with ethidium bromide. Joint molecules were seen only in lane 6. Most of these joint molecules migrated at a position expected of linear dimers (lane 6), but a small portion of the reaction product migrated at a position typical of nicked circular molecules (arrowed). Adding 5 µM dNTPs blocked the reaction completely (lane 7). Table 1 summarizes the effect of transforming *E. coli* with these reaction products.

FIG. 9. Effect of homology length on joint molecule formation. PCR amplified DNAs were prepared containing 4, 6, 8, . . . , 18 bp of end sequence identical to sequences found flanking the NotI site in a pBluescript vector. A mixture of PCR amplified DNA plus NotI-cut vector was incubated with 0. µg of vaccinia DNA polymerase and 0.5 µg of gpI3L for 10 min and then separated by agarose gel electrophoresis (Panel B, inset). The yield of linear-duplex (○) and circular (●) joint molecules in each reaction was determined by densitometry (Panel B). Omitting the polymerase yielded no joint molecules (Δ). The reaction products (plus joint molecules prepared in two additional experiments) were used to transform bacterial SURE cells and the yield of recombinants determined as in Table I (Panel A).

FIG. 10 provides a map of DNA to be recombined to clone a recombinant DNA pRP406-SFV using the method of the invention.

Figure 11:
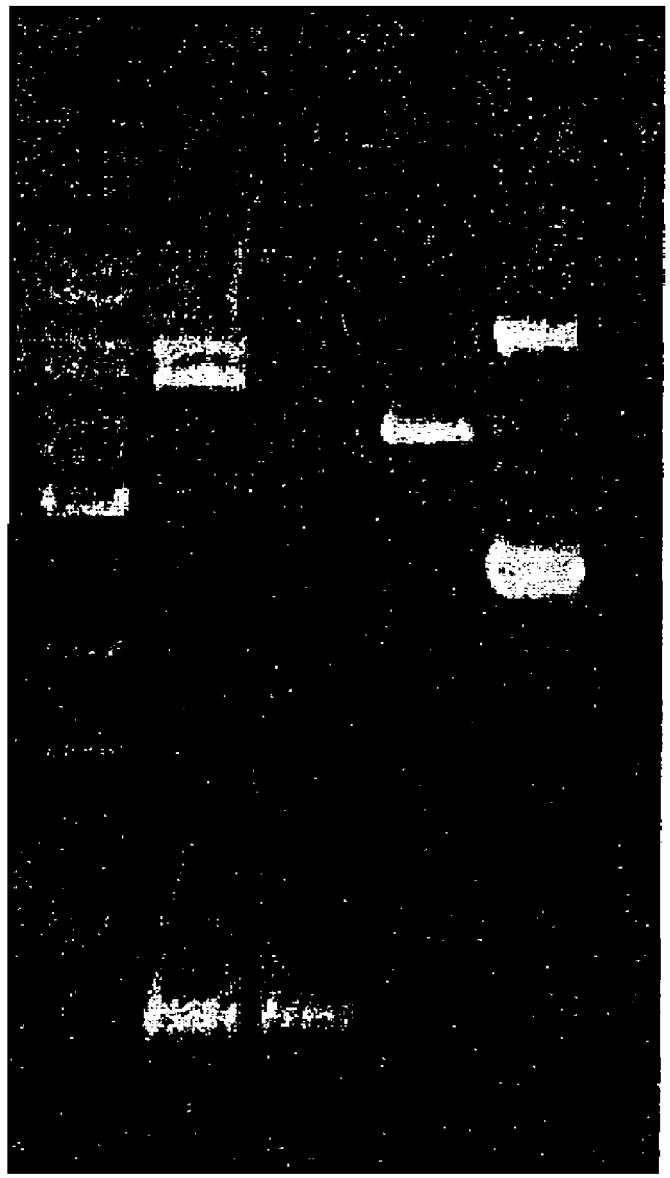
FIG. 11 shows the results of in vitro recombination of the linear DNA shown in FIG. 10 (0.8 % agarose gel).

FIG. 11 shows the results of in vitro recombination of the linear DNA shown in FIG. 10 (shown on 0.8 % agarose gel). After the joining reaction, 1 ul of reaction solution was used for transformation. The rest of solution was deproteinized and electrophoresized.

We claim:

1. A single step method of joining two or more linear duplex DNA molecules comprising incubating two or more linear duplex DNA molecules, each having an x and x' strand of opposite polarities, wherein the 5' end of the x' strand of one linear duplex DNA molecule comprises a sequence of nucleotides that are complementary between about 5 and about 100 nucleotides to the 5' end of the x strand of the linear duplex DNA molecule to which it is to be joined, wherein said incubation is in the presence of a DNA polymerase under conditions whereby the two or more linear duplex DNA molecules are joined, the DNA polymerase has intrinsic 3'-5' exonuclease activity and joins the DNA molecules in an exonuclease-mediated reaction that is mediated by said DNA polymerase and said two or more linear duplex DNA molecules have 5'-overhanging, 3'-overhanging and/or blunt ends.

2. A single step method of joining two or more linear duplex DNA molecules comprising incubating two or more linear duplex DNA molecules, each having an x and x' strand of opposite polarities, wherein the 5' end of the x' strand of one linear duplex DNA molecule comprises a sequence of nucleotides that is complementary to the 5' end of the x strand of the linear duplex DNA molecule to which it is to be joined, wherein said incubation is in the presence of a DNA polymerase under conditions whereby the two or more linear duplex DNA molecules are joined, the DNA polymerase has intrinsic 3'-5' exonuclease activity and joins the DNA molecules in an exonuclease-mediated reaction that is mediated by said DNA polymerase and said two or more linear duplex DNA molecules have 5'-overhanging, 3'-overhanging and/or blunt ends, wherein the DNA polymerase is encoded by a virus.

3. The method according to claim 2, wherein the virus is a poxvirus, herpes virus, adenovirus, Iridovirus or Bacculovirus.

4. The method according to claim 3, wherein the virus is a poxvirus.

5. The method according to claim 4, wherein the virus is vaccinia virus.

6. The method according to claim 2, wherein the DNA polymerase comprises vaccinia virus DNA polymerase.

7. The method according to claim 2, wherein the two or more linear duplex DNA molecules are incubated in the presence of a DNA polymerase and a stimulatory factor.

8. The method according to claim 7, wherein the stimulatory factor is a single strand DNA binding protein.

9. The method according to claim 8, wherein the single strand DNA binding protein is selected from vaccinia virus single strand DNA binding protein, E. coli single strand DNA binding protein, Herpes simplex virus ICP8 protein, yeast replication protein A (yRPA) and human replication protein A (hRPA).

10. The method according to claim 9, wherein the single strand DNA binding protein is vaccinia virus single strand DNA binding protein.

11. The method according to claim 1, wherein the length of the sequence of complementary nucleotides on each linear duplex DNA molecule is between about 8 and about 50 nucleotides.

12. The method according to claim 1, wherein the length of the sequence of complementary nucleotides on each linear DNA molecule is between about 10 and about 35 nucleotides.

13. The method according to claim 1, wherein the two or more linear duplex DNA molecules are incubated in the presence of the DNA polymerase for a time period in the range of about 5 minutes to about 60 minutes.

14. The method according to claim 1, wherein the two or more linear duplex DNA molecules are incubated in the presence of the DNA polymerase for a time period in the range of about 10 minutes to about 40 minutes.

15. The method according to claim 1, wherein the two or more linear duplex DNA molecules are incubated in the presence of the DNA polymerase for a time period in the range of about 15 minutes to about 30 minutes.

16. The method according to claim 1, wherein the two or more linear duplex DNA molecules are incubated in the presence of the DNA polymerase at a temperature in the range of about 35° C. to about 40° C.

17. The method according to claim 1, wherein the two or more linear duplex DNA molecules are incubated in the presence of the DNA polymerase at a temperature of about 37° C.

18. A method of constructing a recombinant DNA molecule comprising:
providing a linearized vector DNA molecule and a template linear duplex DNA molecule, each having a first and a second end;
providing a first primer DNA molecule having a 5' end that comprises nucleotide sequences that will incorporate nucleotide sequences that are complementary between about 5 and about 100 nucleotides to the first end of the linearized vector molecule onto the first end of the template linear duplex DNA molecule and a 3' end that hybridizes to a suitable location on the first end of the template linear duplex DNA molecule;
providing a second primer DNA molecule having a 5' end that comprises nucleotide sequences that will incorporate nucleotide sequences that are complementary between about 5 and about 100 nucleotides to the second end of the linearized vector molecule onto the second end of the template linear duplex DNA molecule and a 3' end that hybridizes to a suitable location on the second end of the template linear duplex DNA molecule;
amplifying the template linear duplex DNA molecule using the polymerase chain reaction with the first and second primers to provide a PCR amplified product; and directly incubating the PCR amplified product in a single step with the linearized vector DNA molecule in the presence of a DNA polymerase under conditions to generate a recombinant DNA molecule, wherein the DNA polymerase has intrinsic 3'-5' exonuclease activity and inserts the PCR amplified product into the linearized vector DNA molecule in an exonuclease mediated reaction that is mediated by said DNA polymerase and the PCR amplified product and linearized vector DNA molecule have 5'-overhanging, 3'-overhanging and/or blunt ends.

19. A method of constructing a recombinant DNA molecule comprising:

providing a linearized vector DNA molecule and a template linear duplex DNA molecule, each having a first and a second end;

providing a first primer DNA molecule having a 5' end that comprises nucleotide sequences that will incorporate nucleotide sequences that are complementary to the first end of the linearized vector molecule onto the first end of the template linear duplex DNA molecule and a 3' end that hybridizes to a suitable location on the first end of the template linear duplex DNA molecule;

providing a second primer DNA molecule having a 5' end that comprises nucleotide sequences that will incorporate nucleotide sequences that are complementary to the second end of the linearized vector molecule onto the second end of the template linear duplex DNA molecule and a 3' end that hybridizes to a suitable location on the second end of the template linear duplex DNA molecule;

amplifying the template linear duplex DNA molecule using the polymerase chain reaction with the first and second primers to provide a PCR amplified product; and directly incubating the PCR amplified product in a single step with the linearized vector DNA molecule in the presence of a DNA polymerase under conditions to generate a recombinant DNA molecule, wherein the DNA polymerase has intrinsic 3'-5' exonuclease activity and inserts the PCR amplified product into the linearized vector DNA molecule in an exonuclease mediated reaction that is mediated by said DNA polymerase and the PCR amplified product and linearized vector DNA molecule have 5'-overhanging, 3'-overhanging and/or blunt ends, wherein the DNA polymerase is encoded by a virus.

20. The method according to claim 19, wherein the virus is a poxvirus, herpes virus, adenovirus, Iridovirus or Bacculovirus.

21. The method according to claim 20, wherein the virus is a poxvirus.

22. The method according to claim 21, wherein the virus is vaccinia virus.

23. The method according to claim 19, wherein the DNA polymerase comprises vaccinia virus DNA polymerase.

24. The method according to claim 19, wherein the PCR amplified product and the linearized vector DNA molecule are incubated in the presence of a DNA polymerase and a stimulatory factor.

25. The method according to claim 24, wherein the stimulatory factor is a single strand DNA binding protein.

26. The method according to claim 25, wherein the single strand DNA binding protein is selected from vaccinia virus single strand DNA binding protein, *E. coli* single strand DNA binding protein, Herpes simplex virus lCP8 protein, yeast replication protein A (yRPA) and human replication protein A (hRPA).

27. The method according to claim 26, wherein the single strand DNA binding protein is vaccinia virus single strand DNA binding protein.

28. The method according to claim 18, wherein the sequence of complementary nucleotides on each linear DNA molecule is between about 8 and about 50 nucleotides.

29. The method according to claim 18, wherein the sequence of complementary nucleotide DNA molecule is between about 10 and about 35 nucleotides.

30. The method according to claim 18, wherein the PCR amplified product and the linearized vector DNA molecule are incubated in the presence of the DNA polymerase for a time period in the range of about 5 minutes to about 60 minutes.

31. The method according to claim 18, wherein the PCR amplified product and the linearized vector DNA molecule are incubated in the presence of the DNA polymerase for a time period in the range of about 10 minutes to about 40 minutes.

32. The method according to claim 18, wherein the PCR amplified product and the linearized vector DNA molecule are incubated in the presence of the DNA polymerase for a time period in the range of about 15 minutes to about 30 minutes.

33. The method according to claim 18, wherein the PCR amplified product and the linearized vector DNA molecule are incubated in the presence of the DNA polymerase at a temperature in the range of about 35° C. to about 40° C.

34. The method according to claim 18, wherein the PCR amplified product and the linearized vector DNA molecule are incubated in the presence of the DNA polymerase at a temperature of about 37° C.

35. The method according to claim 18, wherein the vector transfects a prokaryotic or eukaryotic host cell.

36. The method according to claim 35, wherein the vector is selected from the group consisting of viruses, plasmids, cosmids, phage and BACs.

37. The method according to claim 36, wherein the vector comprises pDW101.

38. A single step method of constructing a recombinant DNA molecule comprising incubating a linearized vector DNA molecule with a linear insert duplex DNA molecule in the presence of a DNA polymerase under conditions whereby the two DNA molecules are joined, wherein the DNA polymerase has intrinsic 3'-5' exonuclease activity and joins the DNA molecules in an exonuclease mediated reaction that is mediated by said DNA polymerase, the linear insert duplex DNA molecule has ends that are complementary between about 5 and about 100 nucleotides to the ends of the linearized vector DNA molecule to which they are to be joined and the linearized vector and linear insert duplex DNA molecules have 5'-overhanging, 3'-overhanging and/or blunt ends.

39. A method of producing a recombinant DNA product comprising transforming the recombinant DNA molecule prepared using the method of claim 18 into a host cell and, optionally, isolating the recombinant DNA product.

40. A method of producing a recombinant DNA product comprising transforming the recombinant DNA molecule prepared using the method of claim 38 into a host cell and, optionally, isolating the recombinant DNA product.

41. A single step method of circularizing single linear duplex DNA molecules having first and second ends, wherein said molecules comprise nucleic acid sequences on said first end that are complementary between about 5 and about 100 nucleotides to nucleic acid sequences on said second end, the method comprising incubating said single linear duplex DNA molecules in the presence of a DNA polymerase under conditions whereby the linear DNA molecules are circularized, wherein the DNA polymerase has intrinsic 3'-5' exonuclease activity and circularizes the DNA molecules in an exonuclease-mediated reaction that is mediated by said DNA polymerase and the linear duplex DNA molecules have 5'-overhanging, 3'-overhanging and/or blunt ends.

42. The method according to claim 41, wherein the linear duplex DNA molecules are obtained by PCR amplifying a linear DNA molecule in the presence of primers that will introduce the complementary nucleic sequences on the first and second ends.

43. The method according to claim 1, wherein the two or more linear duplex DNA molecules have blunt ends.

44. The method according to claim 18, wherein the PCR amplified product and the linearized vector DNA molecules have blunt ends.

45. The method according to claim 38, wherein the linearized vector DNA molecules and the linear insert duplex DNA molecules have blunt ends.

46. The method according to claim 41, wherein the linear duplex DNA molecules have blunt ends.

47. The method according to claim 1, wherein the DNA polymerase joins DNA molecules having 5'overhanging, 3'-overhanging and blunt ends.

48. The method according to claim 18, wherein the DNA polymerase joins DNA molecules having 5'-overhanging, 3'overhanging and blunt ends.

49. The method according to claim 38, wherein the DNA polymerase joins DNA molecules having 5'overhanging, 3'-overhanging and blunt ends.

50. The method according to claim 41, wherein the DNA polymerase joins DNA molecules having 5'overhanging, 3'-overhanging and blunt ends.

51. The method according to claim 1, wherein the sequence of complimentary nucleotides on the 5' end of the x' strand and the sequence of the complimentary nucleotides on the 5' end of the x strand are joined.

52. The method according to claim 18, wherein the sequence of complimentary nucleotides on the PCR amplified product and the sequence of the complementary nucleotides on the linearized vector DNA molecule are joined.

53. The method according to claim 38, wherein the complementary ends on the insert duplex DNA molecule and the linearized vector DNA molecule are joined.

54. The method according to claim 41, wherein the complementary nucleic acid sequences on the first and second ends of the single linear duplex DNA molecule are joined.

55. A single step method of joining two or more linear duplex DNA molecules comprising incubating two or more linear duplex DNA molecules, each having an x and x' strand of opposite polarities, wherein the 5' end of the x' strand of one linear duplex DNA molecule comprises a sequence of nucleotides that are complementary between about 5 and about 100 nucleotides to the 5' end of the x strand of the linear duplex DNA molecule to which it is to be joined, in the presence of a DNA polymerase with intrinsic 3'-5' exonuclease activity, wherein the reaction mixture consists essentially of said two or more linear duplex DNA molecules and said DNA polymerase, the incubation takes place under conditions whereby the two or more linear duplex DNA molecules are joined, the DNA molecules are joined in an exonuclease-mediated reaction that is mediated by said DNA polymerase and said two or more linear duplex DNA molecules have 5'-overhanging, 3'-overhanging and/or blunt ends.

* * * * *